United States Patent [19]

Janulis

[11] Patent Number: 5,082,587
[45] Date of Patent: Jan. 21, 1992

[54] ACHIRAL FLUORINE-CONTAINING LIQUID CRYSTALS

[76] Inventor: Eugene P. Janulis, 3M Center, P.O. Box 34427, St. Paul, Minn. 55133-3427

[21] Appl. No.: 248,948

[22] Filed: Sep. 23, 1988

[51] Int. Cl.$^5$ ............ C09K 19/52; C09K 19/34; C07C 19/08; C07C 69/76
[52] U.S. Cl. ............ 252/299.01; 252/299.61; 252/299.62; 252/299.63; 252/299.67; 560/61; 560/64; 560/100; 560/102; 570/129; 549/369; 549/370; 546/270; 546/272; 546/315; 546/322; 544/298; 544/242; 568/632; 568/331; 568/642
[58] Field of Search ............ 252/299.01, 299.61, 252/299.66, 299.63, 299.66, 299.67, 299.68, 299.62; 560/61, 62, 64, 65, 102, 100; 568/331; 570/129, 130; 544/298, 242; 546/286, 288, 301, 302, 342; 549/369, 370

[56] References Cited

U.S. PATENT DOCUMENTS

| | | | |
|---|---|---|---|
| 3,149,595 | 9/1964 | Zeltner | 112/252 |
| 3,784,608 | 1/1974 | Larson et al. | 71/103 |
| 4,164,412 | 8/1979 | Moore et al. | 568/144 |
| 4,313,878 | 2/1982 | Hsu | 260/340.7 |
| 4,367,924 | 1/1983 | Clark et al. | 350/334 |
| 4,411,494 | 10/1983 | Crossland et al. | 350/339 R |
| 4,419,664 | 12/1983 | Crossland et al. | 340/784 |
| 4,481,149 | 11/1984 | Misaki et al. | 560/61 X |
| 4,510,069 | 4/1985 | Eidenschink et al. | 252/299.61 |
| 4,528,562 | 7/1985 | Crossland et al. | 340/805 |
| 4,614,608 | 9/1986 | LeBarney et al. | 252/299.64 |
| 4,668,427 | 5/1987 | Saito et al. | 252/299.66 |
| 4,886,619 | 12/1989 | Janulis | 252/299.1 |

FOREIGN PATENT DOCUMENTS

| | | |
|---|---|---|
| 0237007 | 9/1987 | European Pat. Off. |
| 0255236 | 2/1988 | European Pat. Off. |
| 2484586 | 11/1981 | France |
| 2168697A | 6/1986 | United Kingdom |

OTHER PUBLICATIONS

Titov, V. et al., "Synthesis and Mesomorphism of Aryl p-Fluoroalkyl (Alkoxy) Benzoates", Molecular Crystal Liquid Crystal, vol. 47 (1978), pp. 1-5.
F. J. Kahn, Appl. Phys. Lett., vol. 22, p. 111 (1973).
Andersson et al., 1st Int'l Symposium on Ferroelectric Liquid Crystals, Bordeaux-Arcachon, France, 1987.
Pelzl, G. et al., Kristall Technik, vol. 14, p. 817 (1979).
Pelzl, G. et al., Mol. Crystl. Liq. Cryst., vol. 53, p. 167 (1979).
Schiller et al., Liquid Crystals, vol. 2, p. 21 (1987).
Pelzl et al., Liquid Crystals, vol. 2, p. 131 (1987).
R. B. Meyer et al. (J. Physique), vol. 36, pp. L-69 (1975).
N. A. Clark et al. (Appl. Phys. Lett.), vol. 36, p. 899 (1980).
Vogel's Textbook of Practical Organic Chemistry, 4th Ed., pp. 645-646, 656 (1978).
Vorbrodt et al., in J. Fur Prakt. Chem., 323, 902-913 (1981).
Introduction to Organic Laboratory Techniques, by Pavia et al., 2nd Ed., p. 32 (1982).
Miyasato et al., Jap. J. Appl. Phys., vol. 22, 1983, pp. 1661 ∝ 1663.
Baikalov et al., Mol. Cryst. Liq. Crystl., 1985, vol. 127, pp. 397–406.
J. W. Goodby & T. M. Leslie, Liquid Crystals & Ordered Fluids, vol. 4, pp. 1-42, Edited by A. C. Griffin & J. P. Johnson.

Primary Examiner—Robert L. Stoll
Assistant Examiner—C. Harris
Attorney, Agent, or Firm—Gary L. Griswold; Walter N. Kirn; Carole Truesdale

[57] ABSTRACT

Achiral fluorine-containing liquid crystal compounds are provided. The compounds comprise a fluorocarbon terminal portion and a hydrocarbon or another fluorocarbon terminal portion, the terminal portions being connected by a central core, the compounds having smectic mesophases or having latent smectic mesophases. The compounds are useful in liquid crystal display devices both along and in mixtures with other materials. Also provided is a process for preparing these compounds.

18 Claims, No Drawings

ACHIRAL FLUORINE-CONTAINING LIQUID CRYSTALS

FIELD OF THE INVENTION

This invention relates to achiral smectic liquid crystals and methods for their preparation. These achiral liquid crystals and mixtures which contain them are useful in a variety of electrooptical displays.

BACKGROUND OF THE INVENTION

Devices employing liquid crystals have found use in a variety of electrooptical applications, in particular those which require compact, energy-efficient, voltage-controlled light valves, such as watch and calculator displays, and flat-panel displays as are found in portable computers and compact televisions.

Liquid crystal displays have a number of unique characteristics, including low voltage and low power of operation, which make them the most promising of the non-emissive electrooptical display candidates currently available. However, slow response and insufficient nonlinearity can impose limitations for many potential applications. The requirement for speed may become especially important in proportion to the number of elements which have to be addressed in a device. This limits the potential use of some types of liquid crystals.

Twisted nematic (TN), supertwisted birefringence effect (SBE), and dynamic scattering (DS), all employing nematic or chiral nematic (cholesteric) liquid crystals, are the modes of liquid crystal displays that are most extensively employed at present. These devices are based upon the dielectric alignment effects (Freedericksz effect) of the nematic and/or chiral nematic liquid crystal or mixtures of nematic or chiral nematic liquid crystals upon application of an electric field. The average molecular long axis of the liquid crystal material takes up a preferred orientation in the applied electric field, the orientation of which is dependent on the sign of the dielectric anisotropy of the material or mixture, and this orientation relaxes upon removal of the applied electric field. This reorientation and relaxation is slow, on the order of a few milliseconds.

Although nematic and chiral nematic liquid crystals are the most extensively employed, there are liquid crystal devices that employ higher ordered smectic liquid crystals.

Devices employing materials with a smectic A mesophase are useful in device applications as described in Crossland, et al. U.S. Pat. Nos. 4,411,494; 4,419,664; and 4,528,562; and F. J. Kahn (Appl. Phys. Lett., vol. 22, p. 111 (1973). These devices are based on the dielectric reorientation of the liquid crystals and response times are on the order of milliseconds.

Mixtures which exhibit a chiral smectic A mesophase are useful in a device as described by Lagerwall, et al. 1st International Symposium On Ferroelectric Liquid Crystals, Bordeaux-Arcachon, France, 1987. These mixtures exhibit an electrooptic effect which is termed a soft-mode ferroelectric effect and sub-microsecond switching can be achieved.

Devices employing materials with a smectic C mesophase are useful in device applications as described by Pelzl, et al. (Kristall Technik., vol. 14, p. 817 (1979); Mol. Cryst. Liq. Cryst., vol. 53, p. 167 (1979); Liquid Crystals, vol. 2, p. 21 (1987); and Liquid Crystals, vol. 2, p. 131 (1987)). These devices are based on the dielectric reorientation of the liquid crystals and the response times are slow.

A recent advance in the liquid crystal art has been the utilization of tilted chiral smectic liquid crystals, which are also termed ferroelectric liquid crystals, in devices which give microsecond switching and bistable operation not possible in any of the device applications described above. Ferroelectric liquid crystals were discovered by R. B. Meyer, et al. (J. Physique, vol 36, pp. 1–69 (1975). A high speed optical switching phenomenon was discovered for the ferroelectric liquid crystals by N. A. Clark, et al. (Appl. Phys. Lett., vol. 36, p. 899 (1980) and U.S. Pat. No. 4,367,924).

The high speed switching of the ferroelectric liquid crystals can be utilized in many applications light valves, displays, printer heads, and the like. In addition to the submicrosecond switching speeds, some ferroelectric device geometries exhibit bistable, threshold sensitive switching, making them candidates for matrix addressed devices containing a large number of elements for passive displays of graphic and pictorial information, as well as, for optical processing applications.

SUMMARY OF THE INVENTION

The present invention provides achiral fluorine-containing liquid crystal compounds comprising a fluorocarbon terminal portion and a hydrocarbon or another fluorocarbon terminal portion, the terminal portions being connected by a central core, the compounds having smectic mesophases or having latent smectic mesophases. Compounds having latent smectic mesophases are those which by themselves do not exhibit a smectic mesophase, but when the compounds are in admixture with said compounds having smectic mesophases or other said compounds having said latent smectic mesophases develop smectic mesophases, under appropriate conditions. The fluorocarbon terminal portion can be represented by the formula $-DC_qF_{2q}X$ where X is hydrogen or fluorine, q is 1-20, and D is $$-\overset{O}{\underset{\|}{C}}-O-(CH_2)_r-, \quad -O-(CH_2)_r-, \quad -(CH_2)_r-, \quad -OSO_2-,$$

$$-SO_2-, \quad -SO_2(CH_2)_r-, \quad -O(CH_2)_r-O(CH_2)_{r'}-,$$

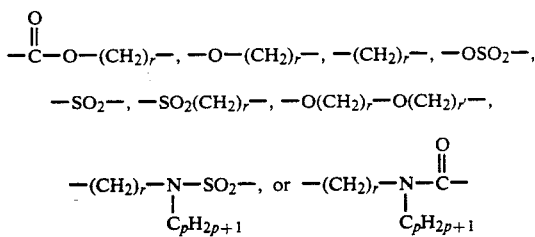

where r and r' are independently 1 to 20 and p is 0 to 4.

In general, the compounds of this invention have a central core comprised of at least two aromatic, heteroaromatic, cycloaliphatic, or substituted aromatic, heteroaromatic, or cycloaliphatic rings. The aromatic or heteroaromatic ring may be selected from fused aromatic, heteroaromatic, or non-fused aromatic or heteroaromatic rings, and the rings may be connected one with another by means of functional groups selected from —COO—, —COS—, —HC=N—, —COSe—. Heteroatoms within the heteroaromatic ring comprise at least one atom selected from N, O, or S.

Achiral fluorine-containing liquid crystal compounds of this invention have a number of desirable properties such as good chemical stability towards water, weak acids and weak bases. They do not undergo degradation during normal use in a liquid crystal display device. They are photochemically stable, that is, they do not easily undergo photochemical reactions. These compounds, due to the novel fluorocarbon terminal portion, have greatly enhanced smectogenic properties, lower birefringences, and lower viscosities than their non-fluroine-containing analogues.

These achiral fluorinated liquid crystals and mixtures which contain them are useful in a variety of electrooptical displays. In particular, these fluorinated materials exhibit smectic mesophases, especially smectic A and C, and are useful in the formulation of smectic A (SmA), smectic C (SmC), chiral smectic A (SmA*), and chiral smectic C (SmC*) mixtures.

Further provided are processes for preparing the achiral fluorine-containing liquid crystal compounds of the invention comprising the steps of (1) mixing at least one compound represented by the formula

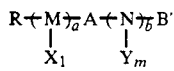

with at least one compound represented by the formula

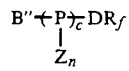

for (2) mixing at least one compound represented by the formula

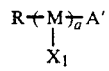

with at least one compound represented by the formula

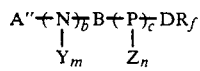

where M, N, and P are each independently

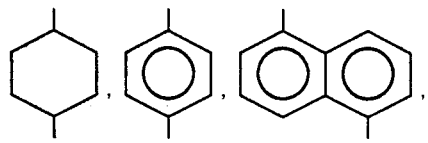

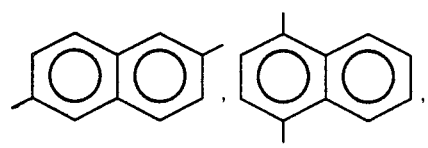

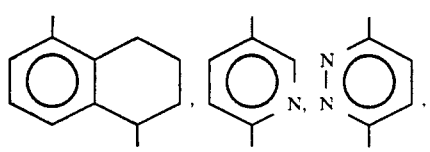

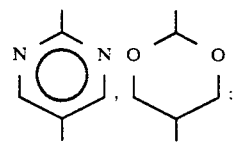

a, b, and c are each independently zero or an integer of from 1 to 3 with the proviso that the sum of a+b+c be at least 2;

each A and B are independently nil,

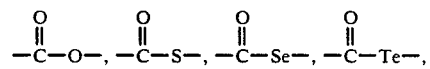

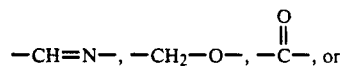

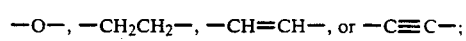

each A', A'', B', and B'' are independently —OH, —COOH, —CH(CH$_2$OH)$_2$, —SH, —SeH, —the, —NH$_2$, —COCl, —CHO, or —CH$_2$COOH with the proviso that A' can enter into an addition or condensation reaction with A'' and B' can enter into an addition or condensation reaction with B'';

each X, Y, and Z are independently —H, —Cl, —F, —OCH$_3$, —OH, —CH$_3$, —NO$_2$, —Br, —I, or —CN;

each l, m and n are independently zero or an integer of 1 to 4;

R is —OC$_q$H$_{2q}$—OC$_{q'}$H$_{2q'+1}$,

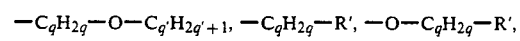

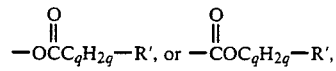

where R' is

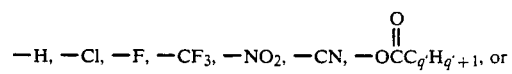

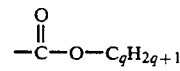

where q and q' are independently 1 to 20;

D is

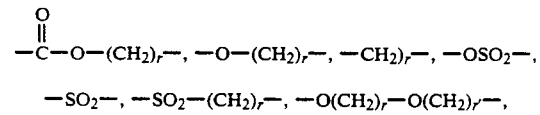

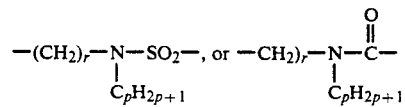

where r and r' are independently 1 to 20, and p is 0 to 4;

R$_f$ is —C$_q$F$_{2q}$—X where X is H or F, and q and q' are independently 1 to 20; and allowing said A' and A'' or B' and B'' to react in the presence of suitable coupling agents.

Still further provided are liquid crystal devices comprising the archiral fluorine-containing liquid crystal compounds of the invention.

DETAILED DESCRIPTION OF THE INVENTION

The present invention relates to achiral fluorine-containing liquid crystal compounds and mixtures derived therefrom which find use in smectic liquid crystal display applications and the like. The liquid crystals of the present invention can be represented by the general formula I:

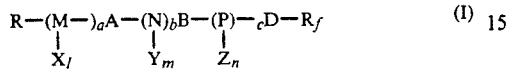

where

M, N, and P are each independently

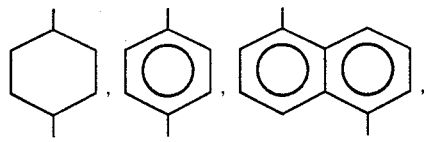

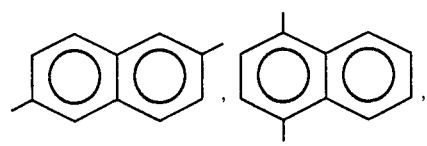

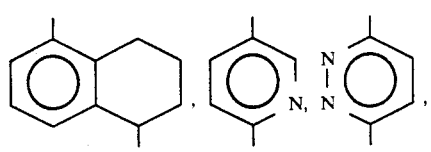

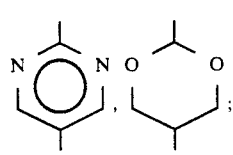

a, b, and c are each independently zero or an integer of from 1 to 3 with the proviso that the sum of a+b+c be at least 2;

each A and B are non-directionally and independently nil,

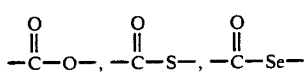

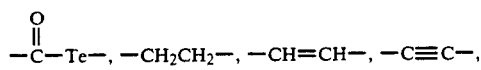

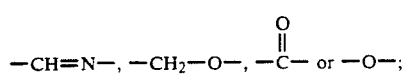

each X, Y, and Z are independently —H, —Cl, —F, —Br, —I, —OH, —OCH$_3$, —CH$_3$, —CN, or —NO$_2$;

each l, m, and n are each independently zero or an integer of 1 to 4,

D is

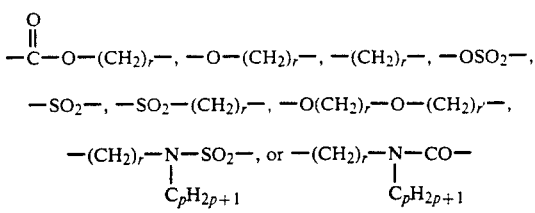

where r and r' are independently 1 to 20, and p is 0 to 4;

R is

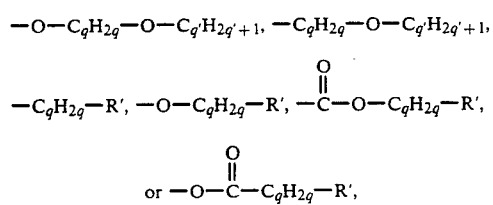

where R' is —Cl, —F, —CF$_3$, —NO$_2$, —CN, —H,

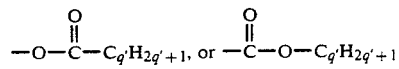

and q and q' are independently 1 to 20, and R can be straight chain or branched, and R$_f$ is C$_q$F$_{2q}$—X where X is H or F, and q and q' are independently 1 to 20.

The birefringence of the materials of this invention are reduced dramatically by the incorporation of fluorine. Materials of the present invention have birefringences typically in the range of 0.05-0.18 depending on the ring systems present and the number of rings, while the corresponding non-fluorine-containing materials have birefringences in the range of 0.10-0.26 for materials which data is available for.

Surprisingly, the smectic liquid crystals of the present invention have suppressed nematic mesophases, i.e. the materials of this invention, because of the incorporation of the novel fluorocarbon terminal portion, exhibit no or very small nematic mesophase temperature ranges are compared to their corresponding non-fluorinated liquid crystal analogues. The liquid crystals of the present invention have enhanced smectic mesophases as compared to their non-fluorine-containing liquid crystal analogues. Thus, the fluorine-containing materials of this invention, when compared to the corresponding non-fluorine-containing analogues, exhibit no or very little nematic liquid crystal behavior and enhanced smectic liquid crystal behavior. This phenomenon of enhanced smectic behavior by the substitution of the partially fluorinated terminal portion of this invention for one or both hydrocarbon terminal portions is general for the materials of this invention.

Chain fluorination induces a higher order in the molecule than the non-fluorine-containing analogs and thus nematic mesophases are lost or greatly narrowed and smectic mesophases are introduced or enhanced. It is believed that the incompatibility of the fluorophilic portions, i.e., the fluorine-containing terminal portions, and the fluorophobic portions, i.e., the hydrocarbon core and terminal portions, of the materials lead to the higher ordering. This belief is supported by the fact that introduction of a hydrogen atom on the terminal carbon portion of a highly fluorinated chain generally results in a narrower smectic phase temperature range due to unfavorable dipole-dipole interactions at the smectic layer interface.

These properties make these materials more suitable for use in smectic liquid crystal device applications than non-fluorine-containing materials. They have broader smectic liquid crystal temperature ranges. The lower birefringence result in less restrictive design parameters than with previously known smectic liquid crystals. The lower viscosity results in faster response times for all of the device applications utilizing the smectic liquid crystal materials of the present invention.

Further, mixtures of the compounds of the invention, with other materials of this invention or with other liquid crystal materials not of this invention or with a combination thereof, can be formulated to provide desired transition temperatures and broad mesophase temperature ranges.

The individual compounds of this invention which exhibit smectic A behavior can be used by themselves or in admixture with other materials, of this invention or not, in smectic A device applications (see Crossland, et al. U.S. Pat. Nos. 4,411,494, 4,419,664, and 4,528,562, which are incorporated herein by reference, and F. J. Kahn (Appl. Phys. Lett., vol. 22, p. 111 (1973). Their low viscosity results in faster reorientation effects compared to their non-fluorine-containing analogues.

The individual compounds of this invention which exhibit smectic C behavior can be used by themselves or in admixture with other materials, of this invention or not, in the smectic C Freedericksz device application described by Pelzl, et al. (see Kristall Technik., vol. 14, p. 817 (1979); Mol. Cryst. Liq. Cryst., vol 53, p. 167 (1979); Liquid Crystals, vol. 2, p. 21 (1987); and Liquid Crystals, vol. 2, p. 131 (1987)). As pointed out in the studies of Pelzl, et al. the decay time in the smectic C phase is shorter than in the nematic phase of the same material and in some cases the rise times are shorter, making this type of device application preferential to utilizing nematics in the classical Freedericksz device mode for some applications. The rise and decay times for the materials examined by Pelzl, et al. were on the order of 2-100 milliseconds for a 50% change in the measured light intensity. For materials of the present invention, rise and decay times of less than 1 millisecond have been observed for an 80% change in the light intensity. Rise and decay times of a few milliseconds for an 80% change in the light intensity have been observed in room temperature mixtures. Devices utilizing materials of the present invention make practical the use of smectic C materials in place of nematic materials in Freedericksz type devices and significantly shorter rise and decay times are attainable.

The compounds of this invention do not show chiral smectic (ferroelectric) liquid crystal behavior by themselves since they are achiral. However, a preferred embodiment of this invention comprises mixtures which contain materials of this invention with at least one chiral (optically active) component. The broad smectic C mesophase ranges of many of the materials of this invention make them useful and desirable as components in the formulation of broad smectic C eutectics, which become ferroelectric, or chiral smectic C, upon addition of a chiral additive.

Other advantages of using the materials of this invention in the formulation of chiral smectic mixtures are the low birefringence and viscosity which can be obtained. The lower viscosity of these materials results in reduced response times for the ferroelectric switching for a given bulk polarization value. The lower birefringence of these materials allows the fabrication of devices with larger device spacings. Light transmission through a surface-stabilized ferroelectric device (as described in U.S. Pat. No. 4,367,924, which is incorporated by reference herein) with two polarizers is represented by the following equation:

$$I = I_o (sin^2(4\theta)) (sin^2(\pi \Delta nd/\lambda))$$

where
$I_o$ = transmission through parallel polarizers
$\theta$ = material tilt angle $\Delta n$ = liquid crystal birefringence d = device spacing $\Delta$ = wavelength of light used To maximize the transmission, both $sin^2 (4\theta)$ and $sin^2(\pi nd/\lambda)$ must be at maximum. This occurs when each term equals one. The first term is a maximum when the tilt angle equals 22.5. This is a function of the liquid crystal and is constant for a given material at a given temperature. The second term is maximum when $\pi \Delta nd = \lambda/2$.

This demonstrates the criticality of the low birefringence of the materials of this invention. Low birefringence allows a larger device thickness, d for a given wavelength of light. Thus, a larger device spacing is possible while still maximizing transmission, allowing easier device construction.

The fluorine-containing precursor compounds are those compounds that are used to synthesize the achiral fluorine containing liquid crystal compounds of this invention. Briefly, commercially available materials were chemically transformed by reaction pathways well-known to those skilled in the art and detailed in the examples. Chemical transformations were comprised of acylation, esterification, etherification, alkylation, and combinations thereof using fluorine-containing and non-fluroine containing chemicals to provide the precursor compounds, which, in turn were caused to react together to yield the achiral fluorine-containing liquid crystal compounds of this invention.

Objects and advantages of this invention are further illustrated by the following examples, but the particular materials and amounts thereof recited in these example, as well as other conditions and details, should not be construed to unduly limit this invention.

In the following examples, all temperatures are in degrees Centigrade and all parts and percentages are by weight unless indicated otherwise. Compounds prepared in the various examples of this invention were characterized by their melting or boiling point and structures were confirmed by using at least one of the methods of analysis: elemental analysis, $^1$H—, $^{19}$F—NMR, IR, and MS spectroscopies.

Examples 1-50 describe procedures for preparing intermediate compounds useful in preparing the liquid crystal compounds of this invention. Examples 51-145 describe preparation of the liquid crystal compounds of this invention. Examples 146-152 describe individual compounds are mixtures incorporating compounds of this invention in liquid crystal devices.

The trifluoroalkylsulfonate esters used in the examples were prepared using the method disclosed in U.S.

Pat. No. 3,149,595 which is incorporated herein by reference, using commercial trifluoromethanesulfonic anhydride in place of trifluoromethanesulfonyl fluoride.

The 4-hexylbenzenethiol used in the examples was prepared using the method described in Vogel's "Textbook of Practical Organic Chemistry", 4th Ed., pp 645-5,656 (1978) from the chlorosulfonation of hexylbenzene with chlorosulfonic acid, and subsequent reduction of the 4-hexylbenzene sulfonyl chloride with $Zn/H_2SO_4$.

The 2-Butyl-1,3-propanediol used in the examples was prepared by the reduction of 2-butyl diethylmalonate with $LiAlH_4$ using the method of Demus, et al. in J. fur Prakt. Chem., 323, 902-913 (1981).

The 4-acetoxybenzoic acid used in the examples was prepared by treatment of 4-hydroxybenzoic acid with acetic anhydride and sulfuric acid catalyst as described in "Introduction to Organic Laboratory Techniques", by Pavia, Lampman, and Kriz, 2nd Edition, pp. 32- 4 (1982).

The trans-4-(trans-4-heptylcyclohexyl)cyclohexane-1-carboxylic acid used in the examples was prepared by base hydrolysis of Merck ZLI-1186 [trans-1-cyano-4-(trans-4'-heptylcyclohexyl)cyclohexane] (Merck & Co., Rahway, NJ),

followed by acidification with aqueous HCl.

The 4-(trans-4-pentylcyclohexyl)benzoic acid used in the examples was prepared by base hydrolysis of Merck ZLI-1114 [1-cyano-4-(trans-4-pentylcylohexyl)benzene)]

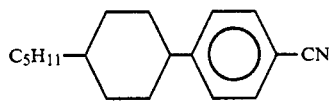

followed by acidification with aqueous HCl.

The 4-decyl-4'-biphenylcarboxylic acid used in the examples was prepared by base hydrolysis of BDH K30 [4-cyano-4 -decylbiphenyl] (British Drug House, Poole, Great Britain)

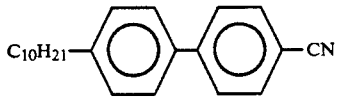

followed by acidification with aqueous HCl.

The 4-decyloxy-4'-biphenylcarboxylic acid used in the examples was prepared by base hydrolysis of BDH M30 [4-cyano-4 '-decyloxybiphenyl] followed by acidification with aqueous HCl.

The trans-5-butyl-2-(4-phenylcarboxylic acid)-1,3-dioxane used in the examples was prepared using the procedure of Hsu in U.S. Pat. No. 4,313,878 which is incorporated herein by reference.

The methyl 3-chloro-4-hydroxybenzoate, methyl 3-methoxy-4- hydroxybenzoate, and methyl 2-chloro-4-hydroxybenzoate used in the examples were synthesized by refluxing the appropriate benzoic acid with an excess of methanol and sulfuric acid catalyst.

The 1,1-dihydroperfluorobutyl 2-chloro-4-hydroxybenzoate used in the examples was synthesized by refluxing 2-chloro-4-hydroxybenzoic acid with an excess of 1,1-dihydroperfluorobutanol and sulfuric acid catalyst.

All acid chlorides used in the examples were prepared by reacting the appropriate carboxylic acid with an excess of thionyl chloride under reflux, followed by removal of the excess thionyl chloride and distillation or recrystallization of the resulting acid chloride.

EXAMPLE 1

Sodium (0.58 g, 25 mg. atoms) was reacted with 25 mL anhydrous methanol at 25° C. until all of the sodium had reacted. Upon completion of the formation of the sodium methylate, methyl 4-hydroxybenzoate (3.8 g, 25 mmol) was added. Excess methanol was removed under reduced pressure and about 25 mL toluene was added and removed under reduced pressure to remove any residual methanol. The solid residue was dissolved in about 100 mL of 2:1 toluene-N,N-dimethylformamide (DMF) and 1,1-dihydroperfluorobutyl trifluoromethylsulfonate (8.3 g, 25 mmol) was added dropwise. The mixture was refluxed for 1 day, allowed to cool, and washed with three 100 mL portions of water. The separated organic layer was dried (anhydrous $MgSO_4$), filtered, and concentrated by reduced pressure The resulting crude methyl 4-(1,1-dihydroperfluorobutoxy)benzoate was refluxed in 100 mL of 10% aqueous sodium hydroxide for 2 hours. The reaction product was cooled and carefully acidified with concentrated aqueous HCl. The precipitated solid was collected by filtration, washed several times with cool water, and purified by recrystallization from ethanol-water to provide, 6.42 g, (80% yield) of product, 4-(1,1-dihydroperfluorobutoxy)benzoic acid.

EXAMPLES 2-16

The compounds of Examples 2-16 were prepared in the same manner as described in Example 1, except that in Example 2, 1,1-dihydroperfluoroethyl trifluoromethylsulfonate (5.80 g, 25 mmol) was substituted for the 1,1-dihydroperfluorobutyl trifluoromethylsulfonate, in Example 3, 1,1-dihydroperfluoropropyl trifluoromethylsulfonate (7.05 g, 25 mmol) was substituted for the 1,1-dihydroperfluorobutyl trifluoromethylsulfonate, in Example 4, 1,1-dihydroperfluorohexyl trifluoromethylsulfonate (10.80 g, 25 mmol) was substituted for the 1,1-dihydroperfluorobutyl trifluoromethylsulfonate, in Example 5, 1,1-dihydroperfluorooctyl trifluoromethylsulfonate (13.30 g, 25 mmol) was substituted for the 1,1-dihydroperfluorobutyl trifluoromethylsulfonate, in Example 6, 1,1,3-trihydroperfluoropropyl trifluoromethylsulfonate (6.60 g, 25 mmol) was substituted for the 1,1-dihydroperfluorobutyl trifluoromethylsulfonate, in Example 7, 1,1,7-trihydroperfluoroheptyl trifluoromethylsulfonate (11.60 g, 25mmol) was substituted for the 1,1-dihydroperfluorobutyl trifluoromethylsulfonate, in Example 8, 1,1-dihydroperfluorohexyl trifluoromethylsulfonate (6.48 g, 15 mmol) was substituted for the 1,1-dihydroperfluorobutyl trifluoromethylsulfonate and methyl 3-chloro-4-hydroxybenzoate (2.79 g, 15 mmol) was substituted for the methyl 4-hydroxybenzoate, in Example 9, 1,1-dihydroperfluorooctyl trifuloromethylsulfonate (5.32 g, 10 mmol) was substituted for the 1,1-dihydroperfluorobutyl trifluoromethylsulfonate and methyl 2-chloro-4-hydroxybenzoate (1,87 g, 10 mmol) was substituted for the methyl 4-hydroxybenzoate, in Example 10, 1,1-dihydroperfluorooctyl trifluoromethylsulfonate (5.32 g, 10 mmol) was substituted for the 1,1-dihydroperfluorobutyl trifluoromethylsulfonate and methyl 3-chloro-4-hydroxybenzoate (1.87 g, 10 mmol) was substituted for the methyl 4-hydroxybenzoate, in Example 11, 1,1-dihydroperfluorohexyl trifluoromethylsulfonate (10.80 g, 25 mmol) was substituted for the 1,1-dihydroperfluorobutyl trifluoromethylsulfonate and methyl 2-chloro-4-hydroxybenzoate (4.66 g, 25 mmol) was substituted for the methyl 4-hydroxybenzoate, in Example 12, 1,1-dihydroperfluorohexyl trifluoromethylsulfonate (12.6 g, 30 mmol) was substituted for the 1,1-dihydroperfluorobutyl trifluoromethylsulfonate and methyl 3-methoxy-4-hydroxybenzoate (5.46 g, 30 mmol) was substituted for the methyl 4-hydroxybenzoate, in Example 13, methyl 2-chloro-4-hydroxybenzoate (7.00 g, 37.5 mmol) was substituted for the methyl 4-hydroxybenzoate and 1,1-dihydroperfluorobutyl trifluoromethylsulfonate was used, (12.45 g, 37.5 mmol), in Example 14, 1-bromooctane (19.3 g, 100 mmol) was substituted for the 1,1-dihydroperfluorobutyl trifluoromethylsulfonate and methyl 3-methoxy-4-hydroxybenzoate (18.2 g, 100 mmol) was substituted for the methyl 4-hydroxybenzoate, in Example 15, 1-bromooctane (19.3 g, 100 mmol) was substituted for the 1,1-dihydroperfluorobutyl trifluoromethylsulfonate and methyl 3-chloro-4-hydroxybenzoate (18.7 g, 100 mmol) was substituted for the methyl 4-hydroxybenzoate, in Example 16, benzyl chloride was substituted for the 1,1-dihydroperfluorobutyl trifluoromethylsulfonate.

The compounds thus produced were 4-(1,1-dihydroperfluoroethoxy)benzoic acid (Example 2), 4-(1,1-dihydroperfluoropropoxy)benzoic acid (Example 3), 4-(1,1-dihydroperfluorohexyloxy)benzoic acid (Example 4), 4-(1,1-dihydroperfluorooctyloxy)benzoic acid (Example 5), 4-(1,1,3-trihydroperfluoropropoxy)benzoic acid (Example 6), 4-(1,1,7-trihydroperfluoroheptyloxy)benzoic acid (Example 7), 3-chloro-4-(1,1-dihydroperfluorohexyloxy)benzoic acid (Example 8), 2-chloro-4-(1,1-dihydroperfluorooctyloxy)benzoic acid (Example 9), 3-chloro-4-(1,1-dihydroperfluorooctyloxy)benzoic acid (Example 10), 2-chloro-4-(1,1-dihydroperfluorohexyloxy)benzoic acid (Example 11), 3-methoxy-4-(1,1-dihydroperfluorohexyloxy)benzoic acid (Example 12), 2-chloro-4-(1,1-dihydroperfluorobutoxy)benzoic acid (Example 13), 3-methoxy-4-octyloxybenzoic acid (Example 14), 3-chloro-4-octyloxybenzoic acid (Example 15), and 4-benzyloxybenzoic acid (Example 16).

EXAMPLE 17

Sodium hydride (2.4 g, 0.1 mol) was suspended in 150 mL dry glyme. Monobenzylhydroquinone (20.0 g, 0.1 mol) was dissolved in 250 mL dry glyme and added dropwise to the sodium hydride suspension with stirring under nitrogen at room temperature. 1-Bromohexane (16.5 g, 0.1 mol) was added dropwise and the reaction mixture was refluxed for 1 day. The reaction product was cooled and the glyme removed under reduced pressure. The residue was dissolved in 300 mL 1:1 ethanol-ethyl acetate and catalytically hydrogenated using 2 g 10% Pd on C and a hydrogen pressure of 500 kPa at room temperature for 4 hours. The catalyst was removed by filtration and the solvent was removed from the filtrate under reduced pressure. The crude product residue was recrystallized from aqueous ethanol to yield 15 g 4-hexyloxyphenol.

EXAMPLES 18–21

In Examples 18-21 which contain alkoxy groups different from those of Example 17 were prepared in the same manner as described in Example 17, except that in Example 18, 1-bromooctane (19.3 g, 100 mmol) was substituted for the 1-bromohexane, in Example 19, 1-bromodecane (22.1 g, 100 mmol) was substituted for the 1-bromohexane, in Example 20, 1-bromododecane (24.9 g, 100 mmol) was substituted for the 1-bromohexane, and in Example 21, 1-bromo-11-(perfluorooctyl)undecane (2.37 g, 5 mmol) was substituted for the 1-bromohexane and 5 mmol sodium hydride and monobenzylhydroquinone were used.

The compounds thus produced were, respectively, 4-octyloxyphenol (Example 18), 4-decyloxyphenol (Example 19), 4-dodecyloxyphenol (Example 20), and 4-(11-perfluorooctylundecyloxy)phenol (Example 21).

EXAMPLE 22

Sodium hydride (5.0 g, 0.21 mol) was suspended in 150 mL dry 1,2-dimethoxyethane (glyme). Monobenzylhydroquinone (40 g, 0.20 mol) was dissolved in 500 mL dry glyme and added dropwise to the sodium hydride with stirring under nitrogen. Upon completion of the addition, the mixture was stirred at room temperature for 1 hour and then cooled to −78° C. 1,1-Dihydroperfluorobutyl trifluoromethylsulfonate (70.0 g, 0.21 mol) was then added dropwise; upon completion of the addition, the reaction was allowed to warm slowly to room temperature. Glyme was removed under reduced pressure. The residue was diluted with 800 mL of water and 700 mL of ethyl ether and mixed vigorously. The separated ether layer was washed twice with about 500 mL 5% sodium hydroxide, twice with about 500 mL water, dried over anhydrous MgSO$_4$, filtered, and concentrated to provide 65 g of a light orange-brown intermediate product. This intermediate product was dissolved in anhydrous ethanol and catalytically hydrogenated using a catalytic amount of 10% Pd/C catalyst and a hydrogen pressure of 500 kPa at room temperature for 2 hours. Catalyst was removed by filtration and ethanol was removed under reduced pressure. The crude phenol was purified by high performance liquid chromatography (HPLC, silica gel, methylene chloride), and the resultant solid was recrystallized from petroleum ether to produce the pure product, 4-(1,1-dihydroperfluorobutoxy)phenol, (59.3% yield).

EXAMPLES 23–30

The compounds in Examples 23-30 which contain different fluorine-containing alkoxy groups from those of Example 22 were prepared in the same manner as described in Example 22, except that in Example 23, 1,1-dihydroperfluorohexyl trifluoromethylsulfonate (45 g, 105 mmol) was substituted for the 1,1-dihydroperfluorobutyl trifluoromethylsulfonate and monobenzylhydroquinone (20.0 g, 100 mmol) was used, in Example 24, 1,1-dihydroperfluorooctyl trifluoromethylsulfonate (58.5 g, 110 mmol) was substituted for the 1,1- dihydroperfluorobutyl trifluoromethylsulfonate and monobenzylhydroquinone (20.0 g, 100 mmol) was used, in Example 25, 1,1,2,2-tetrahydroperfluorohexyl trifluoromethylsulfonate (19.8 g, 50 mmol) was substituted for the 1,1-dihydroperfluorobutyl trifluoromethylsulfonate and monobenzylhydroqunnone (10 g, 50 mmol)

was used, in Example 26, 1,1-dihydroperfluoroethyl trifluoromethylsulfonate (11.6 g, 50 mmol) was substituted for the 1,1-dihydroperfluorobutyl trifluoromethylsulfonate and monobenzylhydroquinone (10 g, 50 mmol) was used, in Example 27, 1,1-dihydroperfluoropropyl trifluoromethylsulfonate (14.1 g, 50 mmol) was substituted for the 1,1-dihydroperfluorobutyl trifluoromethylsulfonate and monobenzylhydroquinone (10 g, 50 mmol) was used, in Example 28, 1,1,3-trihydroperfluoropropyl trifluoromethylsulfonate (13.2 g, 50 mmol) was substituted for the 1,1-dihydroperfluorobutyl trifluoromethylsulfonate and monobenzylhydroquinone (10 g, 50 mmol) was used, in Example 29, 1,1,7-trihydroperfluoroheptyl trifluoromethylsulfonate (8.1 g, 17.5 mmol) was substituted for the 1,1-dihydroperfluorobutyl trifluoromethylsulfonate and monobenzylhydroquinone (3.5 g, 17.5 mmol was used, and in Example 30, 1,1,11-trihydroperfluoroundecyl trifluoromethylsulfonate (3.66 g, 18.3 mmol) was substituted for the 1,1-dihydroperfluorobutyl trifluoromethylsulfonate and monobenzylhydroquinone (4.0 g, 20 mmol) was used.

The compounds thus-produced were 4-(1,1-dihydroperfluorohexyloxy)phenol (Example 23), 4-(1,1-dihydroperfluorooctyloxy)phenol (Example 24), 4-(1,1,2,2-tetrahydroperfluorohexyloxy)phenol (Example 25), 4-(1,1-dihydroperfluoroethoxy)phenol (Example 26), 4-(1,1-dihydroperfluoropropoxy)phenol (Example 27), 4-(1,1,3-trihydroperfluoropropoxy)phenol (Example 28), 4-(1,1,7-trihydroperfluoroheptyloxy)phenol (Example 29), 4-(1,1,11-trihydroperfluoroundecyloxy)phenol (Example 30).

EXAMPLE 31

4-Bromophenol (34.6g, 0.2 mol) was dissolved in 25 mL dry glyme and added dropwise to a suspension of sodium hydride (4.8 g, 0.2 mol) in 25 mL dry glyme. Upon completion of the addition, the mixture was stirred at room temperature for 30 minutes and 25 mL of dry DMF was added. Hexyl bromide (36.3 g, 0.22 mol) was then added and the mixture refluxed for 1 day. The reaction mixture was filtered and the glyme removed under reduced pressure. Methylene chloride (50 mL) was added to the residue and this solution was washed successively with about 50 mL water, about 50 mL 5% sodium hydroxide, about 50 mL water, dried over anhydrous MgSO4, filtered, and concentrated under reduced pressure. Distillation gave 40.5 g (79% yield) of product, 1-bromo-4-hexyloxybenzene, bp 142°-3° C./5mm. Hg.(5 torr).

EXAMPLE 32

Magnesium (2.3 g, 0.1 g. atom) was placed in a 250 mL flask and stirred without solvent for 15 minutes under dry nitrogen. Then dry tetrahydrofuran (THF) (100 mL) was then added to the flask. 1- Bromo-4-hexyloxybenzene (25.7 g, 0.1 mol, example 31) in 50 mL dry THF was placed in an addition funnel and 25% of this solution was added into the flask. This mixture was warmed carefully and once reaction began, the heat was removed and the rate of reflux was controlled by the rate of addition of the remainder of the 1-bromo-4-hexyloxybenzene solution. Upon completion of addition, the reaction mixture was refluxed for 2 hours, cooled to just below reflux and sulfur (3.2 g, 0.1 g. atom) was added very carefully in portions. Upon completion of the addition of the sulfur, the reaction mixture was stirred at room temperature for 3 hours, filtered, and concentrated under reduced pressure. Ethyl ether (200 mL) was added and 1M aqueous HCl was carefully added with vigorous stirring. The separated ether layer was washed with about 100 mL 1M HCl, about 100 mL water, dried over anhydrous MgSO4, filtered, and concentrated under reduced pressure. The crude product was distilled, bp 145° /10 mm, to provide 15.1 g (72% yield) of product, 4-hexyloxythiophenol.

EXAMPLE 33

The compound of Example 33 was prepared using the procedure in Example 32, except that 1-bromoanisole was substituted for the 1-bromo-4-hexyloxybenzene. The compound thus produced was 4-methoxythiophenol.

EXAMPLE 34

Sodium (1.15 g, 50 mg. atoms) was reacted with 50 mL anhydrous methanol, and upon completion of the formation of the sodium methylate, 4-hydroxybenzaldehyde (6.1 g, 50 mmol) was added. Excess methanol was removed under reduced pressure and about 50 mL toluene was added and removed under reduced pressure to remove and residual methanol. The solid residue was dissolved in about 100 mL 2:1 toluene-DMF and 1,1-dihydroperfluorohexyloxy trifluoromethylsulfonate (21.6 g, 50 mmol) was added all at once and the mixture refluxed for 1 day. The reaction product was cooled and washed with three 100 mL portions of water. The separated organic layer was dried over anhydrous MgSO4, filtered, and the filtrate concentrated. Distillation of the concentrate gave 13.1 g (65%) of pure product, 4-(1,1-dihydroperfluorohexyloxy)benzaldehyde, bp 91°-2° C./0.2 torr.

EXAMPLE 35

Sodium hydride (12.0 g, 50 mmol) was suspended in 25 mL diglyme and 2,6-dihydroxynapthalene (25 mmol) in 75 mL diglyme was added. The mixture was warmed for 1 hour at 150° C., then cooled, and 1,1-dihydroperfluorobutyloxy trifluoromethylsulfonate (4.15 g, 12.5 mmol) was added. The mixture was warmed for 2 days at 150° C., then cooled to room temperature. The reaction was acidified with 100 mL 3M HCl and twice extracted with about 100 mL ether. The combined organic extract was washed four times with about 100 mL water, dried over anhydrous MgSO4, filtered, and concentrated. The crude concentrate was purified by HPLC using methylene chloride on a silica gel column to give 1.9 g (44% yield) of product, 6-(1,1-dihydroperfluorobutoxy)-2-napthol.

EXAMPLES 36-37

In Examples 36-37, compounds were prepared in the same manner as described in Example 35, except that in Example 36, 1,4-dihydroxynapthalene (4.00 g, 25 mmol) was substituted for the 2,6-dihydroxynapthalene, in Example 37, 1,5-dihydroxynapthalene (4.00 g, 25 mmol) was substituted for the 2,6-dihydroxynapthalene and 1-bromooctane was substituted for the 1,1-dihydroperfluorobutyl trifluoromethylsulfonate. The compounds thus produced were 4-(1,1-dihydroperfluorobutoxy)-1-napthol (Example 36) and 5-octyloxy-1-napthol (Example 37).

EXAMPLE 38

Sodium (2.3 g, 0.1 g. atom) was added to 100 mL decanol with stirring under nitrogen at room temperature. Upon completion of the reaction, 6-chloronicotinic acid (7.09 g, 0.045 mol) was added and this mixture was refluxed for 2 days. The reaction mixture was acidified with 300 mL 0.5M HCl and the product was extracted 3 times with about 50 mL portions of petroleum ether. The extracts were combined, dried over anhydrous MgSO$_4$, filtered, and the filtrate was concentrated to leave a crude material which was twice recrystallized from heptane to provide 5.2 g (41% yield) of product, 6-decyloxynicotinic acid.

EXAMPLE 39

In this example, a compound was prepared in the same manner as that described in Example 38, except that dl-4-methylhexanol was substituted for the decanol to provide dl-6-(4-methylhexyloxy)nicotinic acid.

EXAMPLE 40

Sodium hydride (1 44 g, 0.06 mol) was suspended in 50 mL dry glyme and 1,1-dihydroperfluorobutanol (6.0 g, 0.03 mol) was added dropwise with stirring under nitrogen at room temperature. Upon completion of the addition, 6-chloronicotinic acid (4.71 g, 0.03 mol), dissolved in 100 mL diglyme with 50 mL cyclohexanone, was added and this mixture was refluxed for 1 day. The reaction mixture was acidified with 150 mL 0.5M HCl and the product was extracted three times with about 50 ml portions of ethyl ether. The separated ether extracts were combined, dried over anhydrous MgSO$_4$, filtered, and the filtrate was concentrated. The crude material was twice recrystallized from heptane to provide 2.63 g (27% yield) of product, 6-(1,1-dihydroperfluorobutoxy)nicotinic acid, containing a small amount of starting 6-chloronicotinic acid.

EXAMPLE 41

4-Benzyloxyphenol (10.0 g, 0.05 mol), 4-(1,1-dihydroperfluorobutoxy)benzoic acid (16.0 g, 0.05 mol) prepared as in Example 1, and 4-dimethylaminopyridine (0.1 g) were dissolved in 100 ml methylene chloride. Dicyclohexylcarbodiimide (11.0 g, 0.053 mol) was then added in one portion. The reaction mixture was stirred at 25° C. under a nitrogen atmosphere for 12 hours. The reaction product was filtered and the filtrate was washed sequentially with about 100 mL 0.5N hydrochloric acid, about 100 mL 5% aqueous sodium bicarbonate, and about 200 mL water. The organic phase was separated, dried over anhydrous MgSO$_4$, filtered, and the filtrated concentrated to yield 22 g of 4-benzyloxyphenyl 4-(1,1-dihydroperfluorobutoxy)benzoate after recrystallization from ethanol.

EXAMPLES 42-45

In Examples 42-45, compounds were prepared as in Example 41, except that in Example 42, 4-benzyloxybenzoic acid (2.28 g, 10 mmol, Example 16) was substituted for the 4-(1,1-dihydroperfluorobutoxy)benzoic acid and 1,1-dihydroperfluorobutanol (2.00 g, 10 mmol) was substituted for the 4-benzyloxyphenol, in Example 43, 4-benzyloxybenzoic acid (2.28 g, 10 mmol, Example 16) was substituted for the 4-(1,1-dihydroperfluorobutoxy)benzoic acid and 1,1-dihydroperfluorohexanol (3.00 g, 10 mmol) was substituted for the 4-benzyloxyphenol. The compounds thus-produced were 1,1-dihydroperfluorobutyl 4-benzyloxybenzoate (Example 42) and 1,1-dihydroperfluorohexyl 4-benzyloxybenzoate (Example 3).

EXAMPLE 44

4-Benzyloxyphenol (20.0 g. 100 mmol) was dissolved in 200 mL dry ether and 10 mL triethylamine. 4-Decyloxybenzoyl chloride (30.0 g, 100 mmol) was added dropwise with stirring at room temperature under nitrogen. After 1 day of stirring at room temperature under nitrogen atmosphere, 200 mL toluene and 200 mL methylene chloride were added to the reaction mixture. The reaction mixture was then filtered and the filtrate washed twice with 0.5N HCl, once with water, and dried over anhydrous magnesium sulfate, filtered, and concentrated under reduced pressure. The crude product was recrystallized from toluene-ethanol to provide 43.9 g (95% yield) 4-benzyloxyphenyl 4-decyloxybenzoate.

EXAMPLE 45

In Example 45, a compound was prepared as in Example 44 except that monobenzylhydroquinone (10 g, 50 mmol) was used and 4-decylbenzoyl chloride (14.0 g, 50 mmol) was substituted for the 4-decyloxybenzoyl chloride. The thus-produced compound was 4-benzyloxyphenyl 4-decylbenzoate.

EXAMPLE 46

4-Benzyloxyphenyl 4-(1,1-dihydroperfluorobutoxy)benzoate (22 g, 0.0438 mol), prepared as in Example 38, was dissolved in 200 mL of 50:50 by volume ethanol-ethyl acetate and hydrogenated at 500 kP hydrogen pressure over 2.0 g 10% palladium on carbon catalyst at 25° C. for 2 hours. The reaction mixture was filtered to remove catalyst and the filtrate was concentrated under reduced pressure to leave 17.3 g 4-hydroxyphenyl 4-(1,1-dihydroperfluorobutoxy)benzoate.

EXAMPLES 47-50

In Examples 47-50, compounds were prepared as in Example 46, except that in Example 47, 1,1-dihydroperfluorobutyl 4-benzyloxybenzoate prepared as in Example 42 was substituted for the 4-benzyloxyphenyl 4-(1,1-dihydroperfluorobutoxy)benzoate, in Example 48, 1,1-dihydroperfluorohexyl 4-benzyloxybenzoate prepared as in Example 43 was substituted for the 4-benzyloxyphenyl 4-(1,1-dihydroperfluorobutoxy)benzoate, in Example 49, 4-benzyloxyphenyl 4-decyloxybenzoate prepared as in Example 44 was substituted for the 4-benzyloxyphenyl 4-(1,1-dihydroperfluorobutoxy)benzoate, and in Example 50, 4-benzyloxyphenyl 4-decylbenzoate prepared as in Example 45 was substituted for the 4-benzyloxyphenyl 4-(1,1-dihydroperfluorobutoxy)benzoate. The compounds thus-produced were 1,1-dihydroperfluorobutyl 4-hydroxybenzoate (Example 47), 1,1-dihydroperfluorohexyl 4-hydroxybenzoate (Example 48), 4-hydroxyphenyl 4-decyloxybenzoate (Example 49), 4-hydroxyphenyl 4-decylbenzoate (Example 50).

EXAMPLE 51

To a solution of 4-hexyloxythiophenol (1.05 g, 5 mmol; synthesized in Example 32) in 30 mL dry ethyl ether containing 1 mL of dry triethylamine, 4-(1,1-dihydroperfluorobutoxyoxy)benzoic acid chloride (1.70 g, 5 mmol; derived from the material synthesized in Example 1), was added dropwise. The reaction mixture was stirred for 1 day at room temperature at which time it was filtered, the filtrate was washed successively with about 50 mL 0.5 M HCl, about 50 mL water, dried over anhydrous MgSO$_4$, filtered, and the filtrate concentrated under reduced pressure. The crude residue was purified by HPLC (toluene, silica gel) followed by recrystallization from anhydrous ethanol to provide 2.17 g (82% yield) of 4-(1,1-dihydroperfluorohexyloxy)thiolbenzoic acid 4'-hexyloxyphenyl ester (compound 1 of Table I) whose structure was confirmed by proton- and fluorine-nuclear magnetic resonance, mass spectrometry, and infrared spectroscopy.

EXAMPLES 52–53

In Examples 52-53, compounds 2-3 of Table I were prepared as in Example 51 except that the precursor compounds indicated below were substituted for the 4-hexyloxythiophenol and for the 4-(1,1-dihydroperfluorobutoxy)benzoic acid chloride.

Example 52, Compound 2, was prepared from 4-hexylthiophenol and 4-(1,1-dihydroperfluorobutoxy)benzoic acid (Example 1).

Example 53, compound 3, was prepared from 4-methoxythiophenol (Example 33) and 4-(1,1-dihydroperfluorooctyloxy)benzoic acid (Example 5).

EXAMPLE 54

4-Decyloxybenzoic acid (0.70g, 2.5 mmol) and 4-(1,1-dihydroperfluorobutyloxy)phenol (0.73, 2.5 mmol, synthesized in Example 19) were dissolved in 50 mL methylene chloride. 6-(N,N-Dimethylamino)pyridine (0.1 g) was added to the reaction mixture followed by N,N,-dicyclohexylcarbodiimide (0.52 g, 2.5 mmol). The reaction product was stirred at room temperature under nitrogen for 1 day, filtered and washed successively with about 50 mL 0.5 M HCl, about 50 mL 5% sodium bicarbonate, and about 50 mL water. The separated organic layer was dried over anhydrous $MgSO_4$, filtered, and the filtrate concentrated under reduced pressure. The crude material was purified by HPLC (toluene, silica gel) followed by recrystallization from ethanol to provide 1.02 g (74% yield) of 4-decyloxybenzoic acid 4'-(1,1-dihydroperfluorobutyloxy)phenyl ester, (compound 4, Table I) characterized by proton- and fluorine-nuclear magnetic resonance, mass spectrometry, and infrared spectroscopy.

EXAMPLES 55–111

In Examples 55-111, compounds 5-61 of Table I were prepared as in Example 54, except that the precursor compounds indicated below were substituted for the 4-decyloxybenzoic acid and the 4-(1,1-dihydroperfluorobutoxy)-phenol.

Example 55, compound 5, was prepared from 4-decyloxybenzoic acid and 4-(1,1-dihydroperfluoroethoxy)phenol (Example 26).

Example 56, compound 6, was prepared from 4-decyloxybenzoic acid and 4-(1,1-dihydroperfluorohexyloxy)phenol (Example 23).

Example 57, compound 7, was prepared from 4-decyloxybenzoic acid and 4-(1,1-dihydroperfluorooctyloxy)phenol (Example 24).

Example 58, compound 8, was prepared from 4-decyloxybenzoic acid and 4-(1,1,2,2-tetrahydroperfluorohexyloxy)phenol (Example 25).

Example 59, compound 9, was prepared from 4-decyloxybenzoic acid and 4-(1,1,3-trihydroperfluoropropoxy)phenol (Example 28).

Example 60, compound 10, was prepared from 4-decyloxybenzoic acid and 4-(1,1,7-trihydroperfluoroheptyloxy)phenol (Example 29).

Example 61, compound 11, was prepared from 4-hexyloxybenzoic acid and 4-(1,1,11-trihydroperfluoroundecyloxy)phenol (Example 30).

Example 62, compound 12, was prepared from 4-decyloxybenzoic acid and 1-(4-hydroxyphenoxy)-11-perfluorooctylundecane (Example 21).

Example 63, compound 13, was prepared from 4-butoxybenzoic acid and 4-(1,1-dihydroperfluoroethoxy)phenol (Example 26).

Example 64, compound 14, was prepared from 4-butoxybenzoic acid and 4-(1,1-dihydroperfluorohexyloxy)phenol (Example 23).

Example 65, compound 15, was prepared from 4-hexyloxybenzoic acid and 4-(1,1-dihydroperfluorobutyoxy)phenol (Example 22).

Example 66, compound 16, was prepared from 4-hexyloxybenzoic acid and 4-(1,1-dihydroperfluorohexyloxy)phenol (Example 23).

Example 67, compound 17, was prepared from 4-hexyloxybenzoic acid and 4-(1,1-dihydroperfluorooctyloxy)phenol (Example 24).

Example 68, compound 18, was prepared from 4-octyloxybenzoic acid and 4-(1,1-dihydroperfluorobutoxy)phenol (Example 22).

Example 69, compound 19, was prepared from 4-octyloxybenzoic acid and 4-(1,1-dihydroperfluorohexyloxy)phenol (Example 23).

Example 70, compound 20, was prepared from 4-octyloxybenzoic acid and 4-(1,1-dihydroperfluorooctyloxy)phenol (Example 24).

Example 71, compound 21, was prepared from 4-decylbenzoic acid and 4-(1,1-dihydroperfluoroethoxy)phenol (Example 26).

Example 72, compound 22, was prepared from 4-decylbenzoic acid and 4-(1,1-dihydroperfluorohexyloxy)phenol (Example 23).

Example 73, compound 23, was prepared from 4-dodecyloxybenzoic acid and 4-(1,1-dihydroperfluorooctyloxy)phenol (Example 24).

Example 74, compound 24, was prepared from 3-chloro-4-octyloxybenzoic acid (Example 15) and 4-(1,1-dihydroperfluoroethoxy)phenol (Example 26).

Example 75, compound 25, was prepared from 4-(1,1-dihydroperfluoroethoxy)benzoic acid (Example 2) and 4-hexyloxyphenol.

Example 76, compound 26, was prepared from 4-(1,1-dihydroperfluoropropoxy)benzoic acid (Example 3) and 4-hexyloxyphenol.

Example 77, compound 27, was prepared from 4-(1,1-dihydroperfluorobutoxy)benzoic acid (Example 1) and 4-hexyloxyphenol.

Example 78, compound 28, was prepared from 4-(1,1-dihydroperfluorobutoxy)benzoic acid (Example 1) and 4-heptyloxyphenol.

Example 79, compound 29, was prepared from 4-(1,1-dihydroperfluorobutoxy)benzoic acid (Example 1) and 4-octyloxyphenol (Example 18).

Example 80, compound 30, was prepared from 4-(1,1-dihydroperfluorobutoxy)benzoic acid (Example 1) and 4-decyloxyphenol (Example 19).

Example 81, compound 31, was prepared from 4-(1,1-dihydroperfluorobutoxy)benzoic acid (Example 1) and 4-dodecyloxyphenol (Example 20).

Example 82, compound 32, was prepared from 4-(1,1-dihydroperfluorohexyloxy)benzoic acid (Example 4) and 4-hexyloxyphenol.

Example 83, compound 33, was prepared from 4-(1,1-dihydroperfluorohexyloxy)benzoic acid (Example 4) and 4-heptyloxyphenol.

Example 84, compound 34, was prepared from 4-(1,1-dihydroperfluorohexyloxy)benzoic acid (Example 4) and 4-octyloxyphenol (Example 18).

Example 85, compound 35, was prepared from 4-(1,1-dihydroperfluorohexyloxy)benzoic acid (Example 4) and 4-decyloxyphenol (Example 19).

Example 86, compound 36, was prepared from 4-(1,1-dihydroperfluorooctyloxy)benzoic acid (Example 5) and 4-hexyloxyphenol.

Example 87, compound 37, was prepared from 4-(1,1-dihydroperfluorooctyloxy)benzoic acid (Example 5) and 4-octyloxyphenol (Example 18).

Example 88, compound 38, was prepared from 4-(1,1-dihydroperfluorooctyloxy)benzoic acid (Example 5) and 4-decyloxyphenol (Example 19).

Example 89, compound 39, was prepared from 4-(1,1,3-trihydroperfluoropropoxy)benzoic acid (Example 6) and 4-hexyloxyphenol.

Example 90, compound 40, was prepared from 4-(1,1,7-trihydroperfluoroheptyloxy)benzoic acid (Example 7) and 4-hexyloxyphenol.

Example 91, compound 41, was prepared from 3-chloro-4-(1,1-dihydroperfluorohexyloxy)benzoic acid (Example 8) and 4-decyloxyphenol (Example 19).

Example 92, compound 42, was prepared from 2-chloro-4-(1,1-dihydroperfluorohexyloxy)benzoic acid (Example 11) and 4-decyloxyphenol (Example 19).

Example 93, compound 43, was prepared from 3-chloro-4-(1,1-dihydroperfluorohexyloxy)benzoic acid (Example 8) and 4-octyloxyphenol (Example 18).

Example 94, compound 44, was prepared from 2-chloro-4-(1,1-dihydroperfluorohexyloxy)benzoic acid (Example 11) and 4-octyloxyphenol (Example 18).

Example 95, compound 45, was prepared from 3-chloro-4-(1,1-dihydroperfluorooctyloxy)benzoic acid (Example 10) and 4-decyloxyphenol (Example 19).

Example 96, compound 46, was prepared from 2-chloro-4-(1,1-dihydroperfluorooctyloxy)benzoic acid (Example 9) and 4-decyloxyphenol (Example 19).

Example 97, compound 47, was prepared from 4-octyloxybenzoic acid and 1,1-dihydroperfluorobutyl 2-chloro-4-hydroxybenzoate.

Example 98, compound 48, was prepared from 4-decyloxybenzoic acid and 1,1-dihydroperfluorobutyl 2-chloro-4-hydroxybenzoate.

Example 99, compound 49, was prepared from 3-methoxy-4-(1,1-dihydroperfluorohexyloxy)benzoic acid (Example 12) and 4-decyloxyphenol (Example 19).

Example 100, compound 50, was prepared from 4-(1,1-dihydroperfluorobutoxy)benzoic acid (Example 1) and 4-cyanophenol.

Example 101, compound 51, was prepared from 3-chloro-4-(1,1-dihydroperfluorohexyloxy)benzoic acid (Example 8) and 4-cyanophenol.

Example 102, compound 52, was prepared from 4-(1,1-dihydroperfluorobutoxy)benzoic acid (Example 1) and 4-(1,1-dihydroperfluoroethoxy)phenol (Example 26).

Example 103, compound 53, was prepared from trans-4-pentylcyclohexanecarboxylic acid and 4-(1,1-dihydroperfluorohexyloxy)phenol (Example 23).

Example 104, compound 54, was prepared from trans-4-heptylcyclohexyl-trans-4'-cyclohexanecarboxylic acid and 4-(1,1-dihydroperfluoroethoxy)phenol (Example 26).

Example 105, compound 55, was prepared from trans-4-heptylcyclohexyl-trans-4'-cyclohexanecarboxylic acid and 4-(1,1-dihydroperfluorohexyloxy)phenol (Example 23).

Example 106, compound 56, was prepared from 4-(trans-4-pentylcyclohexyl)benzoic acid and 4-(1,1-dihydroperfluorohexyloxy)phenol (Example 23).

Example 107, compound 57, was prepared from 4-decylbiphenyl-4-carboxylic acid and 4-(1,1-dihydroperfluorobutoxy)phenol (Example 22).

Example 108, compound 58, was prepared from 4-(1,1-dihydroperfluorobutoxy)benzoic acid (Example 1) and 5-octyloxy-1-napthol (Example 37).

Example 109, compound 59, was prepared from 4-(1,1-dihydroperfluorohexyloxy)benzoic acid (Example 4) and 5-octyloxy-1-napthol (Example 37).

Example 110, compound 60, was prepared from 4-decyloxybenzoic acid and 6-(1,1-dihydroperfluorobutoxy)-2-napthol (Example 35).

Example 111, compound 61, was prepared from 4-octyloxybenzoic acid and 4-(1,1-dihydroperfluorobutoxy)-1-napthol (Example 36).

EXAMPLE 112

6-Decyloxynicotinic acid (2.79, 10 mmol), synthesized in Example 38, and 4-(1,1-dihydroperfluorohexyloxy)phenol (3.92, 10 mmol), synthesized in Example 23, were dissolved in 50 mL methylene chloride. 4-(N,N-Dimethylamino)pyridine (0.1 g) was added to the reaction mixture followed by N,N'-dicyclohexylcarbodiimide (2.27 g, 11 mmol). The reaction mixture was refluxed under nitrogen for 1 day, cooled, filtered, and the filtrate was washed successively with about 50 mL 0.5 M HCl, about 50 mL 5% sodium bicarbonate, and about 50 mL water. The separated organic layer was dried over anhydrous MgSO4, filtered, and the filtrate concentrated under reduced pressure. The crude residue was purified by HPLC (toluene, silica gel) followed by recrystallization from heptane to provide 1.05 g (54% yield) of 6-decyloxynicotinic acid 4,-(1,1-dihydroperfluorohexyloxy)phenyl ester (compound 62, Table I) characterized by H- and F-NMR, MS, and IR spectroscopies.

EXAMPLES 113–114

In Examples 113–114, compounds 63–64 of Table I were prepared as in Example 112 except that the precursor compounds indicated below were substituted for the 6-decyloxynicotinic acid and the 4-(1,1-dihydroperfluorohexyloxy)phenol.

Example 113, compound 63, was prepared from 6-(4-methylhexyloxy)nicotinic acid (Example 39) and 4-(1,1-dihydroperfluorobutoxy)phenol (Example 22).

Example 114, compound 64, was prepared from 6-(4-methylhexyloxy)nicotinic acid (Example 39) and 4-(1,1-dihydroperfluorohexyloxy)phenol (Example 23).

EXAMPLE 115

4-(1,1-Dihydroperfluorohexyloxy)benzaldehyde (1.01 g, 2.5mmol), synthesized in Example 34, and 2-butyl-1,3-propanediol (0.33 g, 2.5mmol) were dissolved in 40 mL of toluene containing a catalytic amount of p-toluenesulfonic acid. This mixture was brought to reflux and the water formed was collected as an azeotrope in a Dean-Stark water trap. After 4 hours the reaction mixture was cooled and washed with about 50 mL 5% NaHCO3 and about 50 mL water. The organic phase was dried over anhydrous MgSO4, filtered, and the filtrate concentrated. The residue was recrystallized from anhydrous ethanol to provide 0.7 g (54% yield) of compound 65, Table I, trans-5-butyl-2-(4-(1,1-dihydroperfluorohexyloxy)phenyl) -1,3-dioxane, whose structure was confirmed by H- and F-NMR, MS, and IR spectroscopies.

EXAMPLE 116

Trans-5-butyl-2-(4-phenylcarboxylic acid)-1,3-dioxane (0.26 g, 1.0 mmol), 4-(1,1-dihydroperfluorobutoxy)-phenol (0.29 g, 1.0 mmol, synthesized in Example 22), and 4-dimethylaminopyridine (0.01 g) were dissolved in 25 mL of methylene chloride and dicyclohexylcarbodiimide (0.22 g, 1.1 mmol) was added all at once. The resulting solution was stirred at room temperature under a nitrogen atmosphere for 1 day. The reaction mixture was filtered and the filtrate was washed successively with about 25 mL 0.5 M HCl, about 25 mL 5% sodium bicarbonate, and about 25 mL water. The separated organic layer was dried over anhydrous MgSO$_4$, filtered, and the filtrate was concentrated under reduced pressure. The crude material was purified by recrystallization from ethanol to provide 0.30 g (56% yield) of compound 66, Table I, trans-5-butyl-2-[4-[4-(1,1-dihydroperfluorohexyloxy)phenyloxycarbonyl]-phenyl]-1,3-dioxane, whose structure was confirmed by H- and F-NMR, MS, and IR spectroscopies.

EXAMPLE 117

In Example 117, compound 67 of Table I was prepared as in Example 116 except that 4-(1,1-dihydroperfluorohexyloxy)phenol (Example 23) was substituted for the 4-(1,1-dihydroperfluorobutoxy)phenol.

EXAMPLE 118

This compound was prepared by two different procedures, A and B below.

Procedure A. 1,1-Dihydroperfluorobutyl 4-hydroxybenzoate (1.60 g, 5 mmol, prepared in Example 47), was dissolved in 50 mL anhydrous ether. Triethylamine (1.0 g) was added followed by the dropwise addition of 4-octyloxybenzoyl chloride (1.34 g, 5 mmol). The reaction mixture was stirred for 1 day under a nitrogen atmosphere at room temperature. The reaction mixture was filtered, the filtrate was washed with about 50 mL 0.5N HCl, about 50 mL water, and the separated organic phase was dried over anhydrous MgSO$_4$, filtered, and the filtrate concentrated. The crude product was recrystallized from ethanol to provide 2.03 g (74% yield) of compound 68, Table I, 4-(4-octyloxybenzoyloxy)benzoic acid 1,1-dihydroperfluorobutoxy ester, whose structure was confirmed by H- and F-NMR, MS, and IR spectroscopies.

Procedure B. Compound 68 was also prepared as in Example 54. 4-Octyloxybenzoic acid (1.25 g, 5 mmol), 1,1-dihydroperfluorobutyl 4-hydroxybenzoate (1.60 g, 5 mmol), and 4-dimethylaminopyridine (0.05 g) were dissolved in 50 mL of methylene chloride. Dicyclohexylcarbodiimide (1.03 g, 5 mmol) was added all at once. The reaction mixture was stirred at room temperature under nitrogen for 1 day, filtered, and the filtrate was washed successively with about 50 mL 0.5 M HCl, about 50 mL 5% sodium bicarbonate, and about 50 mL water. The separated organic layer was dried over anhydrous MgSO$_4$, filtered, and the filtrate concentrated under reduced pressure to leave a crude material which was purified by recrystallization from ethanol to provide 2.07 g (76% yield) of compound 68, Table I, 4-(4-octyloxybenzoyloxy)-benzoic acid 1,1-dihydroperfluorobutoxy ester.

EXAMPLES 119-125

In Examples 119-125, compounds 69-75 of Table I were prepared as in Example 118 except that the precursor compounds indicated below were substituted for the 4-octyloxybenzoic acid chloride and the 1,1-dihydroperfluorobutyl 4-hydroxybenzoate.

Example 119, compound 69, was prepared according to Procedure A from 4-decyloxybenzoyl chloride and 1,1-dihydroperfluorobutyl 4-hydroxybenzoate (Example 47).

Example 120, compound 70, was prepared according to Procedure A from 4-decyloxybenzoyl chloride and 1,1-dihydroperfluorohexyl 4-hydroxybenzoate (Example 48).

Example 121, compound 71, was prepared according to Procedure A from 4-decylbenzoyl chloride and 1,1-dihydroperfluorobutyl 4-hydroxybenzoate (Example 47).

Example 122, compound 72, was prepared according to Procedure B from 6-(4-methylhexyloxy)nicotinic acid (Example 41) and 1,1-dihydroperfluorobutyl 4-hydroxybenzoate (example 47).

Example 123, compound 73, was prepared according to Procedure B from 3-chloro-4-octyloxybenzoic acid (Example 15) and 1,1-dihydroperfluorobutyl 4-hydroxybenzoate (Example 47).

Example 124, compound 74, was prepared according to Procedure B from 4-(1,1-dihydroperfluorobutoxy)-benzoic acid (Example 1) and methyl 4-hydroxybenzoate.

Example 125, compound 75, was prepared according to Procedure B from 4-acetoxybenzoic acid and 4-(1,1-dihydroperfluorobutoxy)phenol (Example 22).

EXAMPLE 126

4-Hydroxyphenyl 4-(1,1-dihydroperfluorobutoxy)-benzoate (2.06 g, 5 mmol, synthesized in Example 46), and triethylamine (2.00 g) were dissolved in 50 mL anhydrous THF. 4-Octyloxybenzoyl chloride (1.34 g, 5 mmol) was added dropwise with stirring. Upon completion of the addition, the reaction mixture was stirred at room temperature under a nitrogen atmosphere for 1 day. The reaction mixture was filtered and the filtrate was concentrated under reduced pressure The crude residue was recrystallized from toluene-ethanol to give 2.93 g, (91%) of compound 76, Table I,1-(4-octyloxybenzoyloxy)-4-(4-(1,1-dihydroperfluorobutoxy)benzoyloxy)benzene.

EXAMPLES 127-135

In Examples 127-135, compounds 77-85 of Table I were prepared as in Example 126 except that the precursor compounds indicated below were substituted for the 4-octyloxybenzoyl chloride and 4-hydroxyphenyl 4-(1,1-dihydroperfluorobutoxy)benzoate.

Example 127, compound 77, was prepared from 4-decyloxybenzoyl chloride and 4-hydroxyphenyl 4-(1,1-dihydroperfluorobutoxy)benzoate (Example 46).

Example 128, compound 78, was prepared from 4-decylbenzoyl chloride and 4-hydroxyphenyl 4-(1,1-dihydroperfluorobutoxy)benzoate (Example 46).

Example 129, compound 79, was prepared from 3-chloro-4-octyloxybenzoyl chloride (Example 15) and 4-hydroxyphenyl 4-(1,1-dihydroperfluorobutoxy)benzoate (Example 46).

Example 130, compound 80, 3-methoxy-4-octyloxybenzoyl chloride (Example 14) and 4-hydroxyphenyl 4-(1,1-dihydroperfluorobutoxy)benzoate (Example 46).

Example 131, compound 81, was prepared from 6-(4-methylhexyloxy)nicotinoyl chloride (Example 39) and 4-hydroxyphenyl 4-(!,!-dihydroperfluorobutoxy)benzoate (Example 46).

Example 132, compound 82, was prepared from 4-(1,1-dihydroperfluoroethoxy)phenol (Example 26) and 3-chloro-4-(4'-decyloxybenzyloxyl)benzoic acid.

Example 133, compound 83, was prepared from 2-chloro-4-(1,1-dihydroperfluorohexyloxy)benzoyl chloride (Example 11) and 4-hydroxyphenyl 4-decylbenzoate (Example 50).

Example 134, compound 84, was prepared from 3-chloro-4-(1,1-dihydroperfluorohexyloxy)benzoyl chloride (Example 8) and 4-hydroxyphenyl 4-decylbenzoate (Example 50).

Example 135, compound 85, was prepared from 4-(1,1-dihydroperfluorooctyloxy)benzoic acid (Example 5) and 4-hydroxyphenyl 4-(1,1-dihydroperfluorobutoxy)benzoate (Example 46).

Example 136

Hydroquinone (0.55 g, 5 mmol), 4-(1,1-dihydroperfluorobutoxy)benzoic acid (3.20 g, 10.0 mmol, prepared in Example 1), and 4-dimethylaminopyridine (0.10 g) were dissolved in 100 mL of methylene chloride. Dicyclohexylcarbodiimide (2.06 g, 10 mmol) was then added all at once. The reaction mixture was stirred at room temperature under nitrogen for 1 day, filtered, and washed successively with about 100 mL 0.5 M HCl, about 100 ml 5% sodium bicarbonate, and about 100 mL water. The separated organic layer was dried over anhydrous $MgSO_4$, filtered, and the filtrate concentrated under reduced pressure. The crude material was purified by recrystallization from ethanol-toluene to provide 2.62 g (73% yield) of compound 86, Table I, 1,4-bis-(4-(1,1-dihydroperfluorobutoxy)benzoyloxy)benzene, whose structure was confirmed by H- and F-NMR, MS, and IR spectroscopies.

EXAMPLES 137–141

In Examples 137 compounds 87-91 of Table I were prepared as in Example 124 except that the precursor compounds indicated below were substituted for the hydroquinone and 4-(1,1-dihydroperfluorobutoxy)benzoic acid Example 137, compound 87, was prepared from chlorohydroquinone and 4-(1,1-dihydroperfluorohexyloxy)benzoic acid (Example 4).

Example 138, compound 88, was prepared from methylhydroquinone and 4-(1,1-dihydroperfluoropropoxy)benzoic acid (Example 3).

Example 139, compound 89, was prepared from tetrafluorohydroquinone and 4-(1,1-dihydroperfluorobutoxy)benzoic acid (Example 1).

Example 140, compound 90, was prepared from 1,4-dihydroxynapthalene and 4-(1,1-dihydroperfluorobutoxy)benzoic acid (Example 1).

Example 141, compound 91, was prepared from 2,6-dihydroxynapthalene and 4-(1,1-dihydroperfluorobutoxy)benzoic acid (Example 1).

EXAMPLE 142

Terephthaloyl chloride (1.02 g, 5.0 mmol) was added dropwise to a solution of 4-(1,1-dihydroperfluoroethoxy)phenol (1.92 g, 10.0 mmol) prepared in Example 26, 2 mL of triethylamine, and 50 mL of anhydrous THF. Upon completion of the addition, the reaction mixture was stirred at room temperature under a nitrogen atmosphere for 1 day, filtered, and the filtrate was concentrated under reduced pressure The crude residue was recrystallized from toluene-ethanol to provide 2.38 g (93% yield) of compound 92, Table I, bis-(4-(1,1-dihydroperfluoroethoxy)phenyl) terephthalate, whose structure was confirmed by H- and F-NMR, MS, and IR spectroscopies.

EXAMPLES 143–145

In Examples 143-145, compounds 93-95 of Table I were prepared as in Example 142, except that the precursor compounds indicated below were substituted for the (4-(1,1-dihydroperfluoroethoxy)phenol.

Example 143, compound 93, was prepared using 4-(1,1-dihydroperfluoropropoxy)phenol (Example 27).

Example 144, compound 94, was prepared using 4-(1,1-dihydroperfluorobutoxy)phenol (Example 22).

Example 145, compound 95, was prepared using 4-(1,1-dihydroperfluorohexyloxy)phenol (Example 23).

TABLE I

| Cmpd No. | Compound |
| --- | --- |
| 1 | $C_3F_7CH_2O$—⟨phenyl⟩—C(=O)S—⟨phenyl⟩—$OC_6H_{13}$ |
| 2 | $C_3F_7CH_2O$—⟨phenyl⟩—C(=O)S—⟨phenyl⟩—$C_6H_{13}$ |
| 3 | $C_7F_{15}CH_2O$—⟨phenyl⟩—C(=O)S—⟨phenyl⟩—$OCH_3$ |
| 4 | $C_3F_7CH_2O$—⟨phenyl⟩—OC(=O)—⟨phenyl⟩—$OC_{10}H_{21}$ |

TABLE I-continued

| Cmpd No. | Compound |
|---|---|
| 5 | CF₃CH₂O—⟨⟩—OC(=O)—⟨⟩—OC₁₀H₂₁ |
| 6 | C₅F₁₁CH₂O—⟨⟩—OC(=O)—⟨⟩—OC₁₀H₂₁ |
| 7 | C₇F₁₅CH₂O—⟨⟩—OC(=O)—⟨⟩—OC₁₀H₂₁ |
| 8 | C₄F₉(CH₂)₂O—⟨⟩—OC(=O)—⟨⟩—OC₁₀H₂₁ |
| 9 | H(CF₂)₂CH₂O—⟨⟩—OC(=O)—⟨⟩—OC₁₀H₂₁ |
| 10 | H(CF₂)₆CH₂O—⟨⟩—OC(=O)—⟨⟩—OC₁₀H₂₁ |
| 11 | H(CF₂)₁₀CH₂O—⟨⟩—OC(=O)—⟨⟩—OC₆H₁₃ |
| 12 | C₈F₁₇(CH₂)₁₁O—⟨⟩—OC(=O)—⟨⟩—OC₁₀H₂₁ |
| 13 | CF₃CH₂O—⟨⟩—OC(=O)—⟨⟩—OC₄H₉ |
| 14 | C₅F₁₁CH₂O—⟨⟩—OC(=O)—⟨⟩—OC₄H₉ |
| 15 | C₃F₇CH₂O—⟨⟩—OC(=O)—⟨⟩—OC₆H₁₃ |
| 16 | C₅F₁₁CH₂O—⟨⟩—OC(=O)—⟨⟩—OC₆H₁₃ |
| 17 | C₇F₁₅CH₂O—⟨⟩—OC(=O)—⟨⟩—OC₆H₁₃ |

TABLE I-continued

| Cmpd No. | Compound |
|---|---|
| 18 | $C_3F_7CH_2O-\bigcirc-OC(=O)-\bigcirc-OC_8H_{17}$ |
| 19 | $C_5F_{11}CH_2O-\bigcirc-OC(=O)-\bigcirc-OC_8H_{17}$ |
| 20 | $C_7F_{15}CH_2O-\bigcirc-OC(=O)-\bigcirc-OC_8H_{17}$ |
| 21 | $CF_3CH_2O-\bigcirc-OC(=O)-\bigcirc-C_{10}H_{21}$ |
| 22 | $C_5F_{11}CH_2O-\bigcirc-OC(=O)-\bigcirc-C_{10}H_{21}$ |
| 23 | $C_7F_{15}CH_2O-\bigcirc-OC(=O)-\bigcirc-OC_{12}H_{25}$ |
| 24 | $CF_3CH_2O-\bigcirc-OC(=O)-\bigcirc(Cl)-OC_8H_{17}$ |
| 25 | $CF_3CH_2O-\bigcirc-C(=O)O-\bigcirc-OC_6H_{13}$ |
| 26 | $C_2F_5CH_2O-\bigcirc-C(=O)O-\bigcirc-OC_6H_{13}$ |
| 27 | $C_3F_7CH_2O-\bigcirc-C(=O)O-\bigcirc-OC_6H_{13}$ |
| 28 | $C_3F_7CH_2O-\bigcirc-C(=O)O-\bigcirc-OC_7H_{15}$ |
| 29 | $C_3F_7CH_2O-\bigcirc-C(=O)O-\bigcirc-OC_8H_{17}$ |
| 30 | $C_3F_7CH_2O-\bigcirc-C(=O)O-\bigcirc-OC_{10}H_{21}$ |

TABLE I-continued

| Cmpd No. | Compound |
|---|---|
| 31 | $C_3F_7CH_2O\text{-}\bigcirc\text{-}CO\text{-}O\text{-}\bigcirc\text{-}OC_{12}H_{25}$ |
| 32 | $C_5F_{11}CH_2O\text{-}\bigcirc\text{-}CO\text{-}O\text{-}\bigcirc\text{-}OC_6H_{13}$ |
| 33 | $C_5F_{11}CH_2O\text{-}\bigcirc\text{-}CO\text{-}O\text{-}\bigcirc\text{-}OC_7H_{15}$ |
| 34 | $C_5F_{11}CH_2O\text{-}\bigcirc\text{-}CO\text{-}O\text{-}\bigcirc\text{-}OC_8H_{17}$ |
| 35 | $C_5F_{11}CH_2O\text{-}\bigcirc\text{-}CO\text{-}O\text{-}\bigcirc\text{-}OC_{10}H_{21}$ |
| 36 | $C_7F_{15}CH_2O\text{-}\bigcirc\text{-}CO\text{-}O\text{-}\bigcirc\text{-}OC_6H_{13}$ |
| 37 | $C_7F_{15}CH_2O\text{-}\bigcirc\text{-}CO\text{-}O\text{-}\bigcirc\text{-}OC_8H_{17}$ |
| 38 | $C_7F_{15}CH_2O\text{-}\bigcirc\text{-}CO\text{-}O\text{-}\bigcirc\text{-}OC_{10}H_{21}$ |
| 39 | $H(CF_2)_2CH_2O\text{-}\bigcirc\text{-}CO\text{-}O\text{-}\bigcirc\text{-}OC_6H_{13}$ |
| 40 | $H(CF_2)_6CH_2O\text{-}\bigcirc\text{-}CO\text{-}O\text{-}\bigcirc\text{-}OC_6H_{13}$ |
| 41 | $C_5F_{11}CH_2O\text{-}\bigcirc(Cl)\text{-}CO\text{-}O\text{-}\bigcirc\text{-}OC_{10}H_{21}$ |
| 42 | $C_5F_{11}CH_2O\text{-}\bigcirc(Cl)\text{-}CO\text{-}O\text{-}\bigcirc\text{-}OC_{10}H_{21}$ |

TABLE I-continued

| Cmpd No. | Compound |
|---|---|
| 43 | $C_5F_{11}CH_2O$—[Ph(Cl)]—CO—O—[Ph]—$OC_8H_{17}$ (Cl meta to ester, para to ether) |
| 44 | $C_5F_{11}CH_2O$—[Ph(Cl)]—CO—O—[Ph]—$OC_8H_{17}$ (Cl ortho to CO) |
| 45 | $C_7F_{15}CH_2O$—[Ph(Cl)]—CO—O—[Ph]—$OC_{10}H_{21}$ |
| 46 | $C_7F_{15}CH_2O$—[Ph(Cl)]—CO—O—[Ph]—$OC_{10}H_{21}$ |
| 47 | $C_3F_7CH_2OOC$—[Ph(Cl)]—O—CO—[Ph]—$OC_8H_{17}$ |
| 48 | $C_3F_7CH_2OOC$—[Ph(Cl)]—O—CO—[Ph]—$OC_{10}H_{21}$ |
| 49 | $C_5F_{11}CH_2O$—[Ph($OCH_3$)]—CO—O—[Ph]—$OC_{10}H_{21}$ |
| 50 | $C_3F_7CH_2O$—[Ph]—CO—O—[Ph]—$C\equiv N$ |
| 51 | $C_5F_{11}CH_2O$—[Ph(Cl)]—CO—O—[Ph]—$C\equiv N$ |
| 52 | $C_3F_7CH_2O$—[Ph]—CO—O—[Ph]—$OCH_2CF_3$ |
| 53 | $C_5F_{11}CH_2O$—[Ph]—O—CO—[Cy]—$C_5H_{11}$ |

TABLE I-continued

| Cmpd No. | Compound |
|---|---|
| 54 | $CF_3CH_2O-$⌬$-O-\overset{O}{\underset{\|}{C}}-$⬡$-$⬡$-C_7H_{15}$ |
| 55 | $C_5F_{11}CH_2O-$⌬$-O-\overset{O}{\underset{\|}{C}}-$⬡$-$⬡$-C_7H_{15}$ |
| 56 | $C_5F_{11}CH_2O-$⌬$-O-\overset{O}{\underset{\|}{C}}-$⌬$-$⬡$-C_5H_{11}$ |
| 57 | $C_3F_7CH_2O-$⌬$-O-\overset{O}{\underset{\|}{C}}-$⌬$-$⌬$-C_{10}H_{21}$ |
| 58 | $C_3F_7CH_2O-$⌬$-\overset{O}{\underset{\|}{C}}-O-$(naphthyl)$-OC_8H_{17}$ |
| 59 | $C_5F_{11}CH_2O-$⌬$-\overset{O}{\underset{\|}{C}}-O-$(naphthyl)$-OC_8H_{17}$ |
| 60 | $C_3F_7CH_2O-$(naphthyl)$-O-\overset{O}{\underset{\|}{C}}-$⌬$-OC_{10}H_{21}$ |
| 61 | $C_3F_7CH_2O-$(naphthyl)$-O-\overset{O}{\underset{\|}{C}}-$⌬$-OC_8H_{17}$ |
| 62 | $C_5F_{11}CH_2O-$⌬$-O-\overset{O}{\underset{\|}{C}}-$(pyridyl)$-OC_{10}H_{21}$ |
| 63 | $C_3F_7CH_2O-$⌬$-O-\overset{O}{\underset{\|}{C}}-$(pyridyl)$-O(CH_2)_3CHC_2H_5$<br>$\hspace{6cm}\|$<br>$\hspace{6cm}CH_3$ |
| 64 | $C_5F_{11}CH_2O-$⌬$-O-\overset{O}{\underset{\|}{C}}-$(pyridyl)$-O(CH_2)_3CHC_2H_5$<br>$\hspace{6cm}\|$<br>$\hspace{6cm}CH_3$ |

TABLE I-continued

| Cmpd No. | Compound |
|---|---|
| 76 | $C_3F_7CH_2O$—⌬—CO-O—⌬—O-OC—⌬—$OC_8H_{17}$ |
| 77 | $C_3F_7CH_2O$—⌬—CO-O—⌬—O-OC—⌬—$OC_{10}H_{21}$ |
| 78 | $C_3F_7CH_2$—⌬—CO-O—⌬—O-OC—⌬—$C_{10}H_{21}$ |
| 79 | $C_3F_7CH_2O$—⌬—CO-O—⌬—O-OC—⌬(Cl)—$OC_8H_{17}$ |
| 80 | $C_3F_7CH_2O$—⌬—CO-O—⌬—O-OC—⌬($OCH_3$)—$OC_8H_{17}$ |
| 81 | $C_3F_7CH_2O$—⌬—CO-O—⌬—O-OC—(pyridine N)—$O(CH_2)_3CHC_2H_5$ / $CH_3$ |
| 82 | $CF_3CH_2O$—⌬—CO-O—⌬(Cl)—O-OC—⌬—$OC_{10}H_{21}$ |
| 83 | $C_5F_{11}CH_2O$—⌬(Cl)—CO-O—⌬—O-OC—⌬—$C_{10}H_{21}$ |
| 84 | $C_5F_{11}CH_2O$—⌬(Cl)—CO-O—⌬—O-OC—⌬—$C_{10}H_{21}$ |
| 85 | $C_3F_7CH_2O$—⌬—CO-O—⌬—O-OC—⌬—$OCH_2C_7F_{15}$ |
| 86 | $C_3F_7CH_2O$—⌬—CO-O—⌬—O-OC—⌬—$OCH_2C_3F_7$ |

TABLE I-continued

| Cmpd No. | Compound |
|---|---|
| 87 | $C_5F_{11}CH_2O$—⌬—CO—O—⌬(Cl)—O—OC—⌬—$OCH_2C_5F_{11}$ |
| 88 | $C_2F_5CH_2O$—⌬—CO—O—⌬($CH_3$)—O—OC—⌬—$OCH_2C_2F_5$ |
| 89 | $C_3F_7CH_2O$—⌬—CO—O—⌬(F,F,F,F)—O—OC—⌬—$OCH_2C_3F_7$ |
| 90 | $C_3F_7CH_2O$—⌬—CO—O—(naphthyl)—O—OC—⌬—$OCH_2C_3F_7$ |
| 91 | $C_3F_7CH_2O$—⌬—CO—O—(naphthyl)—O—OC—⌬—$OCH_2C_3F_7$ |
| 92 | $CF_3CH_2O$—⌬—OC—⌬—CO—⌬—$OCH_2CF_7$ |
| 93 | $C_2F_5CH_2O$—⌬—OC—⌬—CO—⌬—$OCH_2C_2F_5$ |
| 94 | $C_3F_7CH_2O$—⌬—OC—⌬—CO—⌬—$OCH_2C_3F_7$ |
| 95 | $C_5F_{11}CH_2O$—⌬—OC—⌬—CO—⌬—$OCH_2C_5F_{11}$ |

Compounds of Table I were evaluated for transition temperatures by optical observation of material phase changes using a Mettler FP-5 hot stage and a leitz polarizing microscope and/or by standard practice differential scanning calorimetry (DSC) using a perkin elmer model DSC-4. The transition temperatures (°C.), upon cooling from the isotropic state (I) to the crystalline state (K), are set forth in Table II. Transitions to and from mesophases other than smectic A (SmA) and smectic C (SmC) are indicated in Table II. The nematic phase is represented by N, smectic B by SmB, smectic E by SmE, and smectic F by SmF.

TABLE II

| Cmpd No. | I→SmA | SmA→SmC | SmA/SmC→K |
|---|---|---|---|
| 1 | 98 | 67 | 29 |
| 2 | 81 | 63 | 52 |
| 3 | 161 | — | 68 |
| 4 | 87 | 61 | 42 |
| 5 | 88 | — | 44 |
| 6 | 93 | 78 | 53 |

TABLE II-continued

| Cmpd No. | I→SmA | SmA→SmC | SmA/SmC→K |
|---|---|---|---|
| 7 | 124 | 104 | 72 |
| 8 | 114 | 79 | 56 |
| 9 | 70 | — | 43 |
| 10 | 76 | 63 | 48 |
| 11 | 97 | — | 91 |
| 12 | 133 | 110 | 76 |
| 13 | 80 | — | 64 |
| 14 | 113 | — | 40 |
| 15 | 106 | 56 | 30 |
| 16 | 127 | 53 | 21 |
| 17 | 140 | 53 | 48 |
| 18 | 96 | 63 | 37 |
| 19 | 112 | 83 | 36 |
| 20 | 135 | 73 | 60 |
| 21 | 67 | — | 55 |
| 22 | 82 | 59 | 47 |
| 23 | 115 | 105 | 77 |
| 24 | 74 (I-K) | — | — |
| 25 | 88 | — | 82 |
| 26 | 78 | — | 61 |
| 27 | 92 | 65 | 59 |
| 28 | 87 | 56 | 49 |
| 29 | 90 | 62 | 46 |
| 30 | 86 | 59 | 54 |
| 31 | 83 | — | 70 |
| 32 | 111 | 69 | 36 |
| 33 | 102 | 63 | 46 |
| 34 | 108 | 84 | 45 |
| 35 | 100 | 85 | 59 |
| 36 | 136 | 79 | 61 |
| 37 | 126 | 88 | 76 |
| 38 | 121 | 102 | 79 |
| 39 | 72 | — | 71 |
| 40 | 73 | 42 | 40 |
| 41 | 76 | 59 | 32 |
| 42 | 57 (I→SmC) | — | 55 |
| 43 | 83 | 59 | 9 |
| 44 | 54 | — | 42 |
| 45 | 98 | 72 | 55 |
| 46 | 84 | 71 | 47 |
| 47 | 50 | 34 | ←20 |
| 48 | 43 | 35 | 9 |
| 49 | 54 | — | 40 |
| 50 | 58 | — | 43 |
| 51 | 124 (I←K) | (SmA on rapid cooling) | |
| 52 | 80 | — | 53 |
| 53 | 95 | 84 (SmA→SmB) | 60 (SmB→K) |
| 54 | 187 (I→N) | 172 (N→SmB) | 67 (SmB→K) |
| 55 | 198 | 195 SmA→SmB) | 68 (SmB→K) |
| 56 | 210 | 121 (SmA→SmB) | 77 (SmB→K) |
| 57 | 185 | 142 | 107 |
| 58 | 59 (I→K) | | |
| 59 | 92 | — | 20 |
| 60 | 137 | 91 | 64 |
| 61 | 92 | — | 30 |
| 62 | 76 | 43 | 38 |
| 63 | 43 | — | 30 |
| 64 | 62 | 33 | 20 |
| 65 | 100 | — | 55 |
| 66 | 200 | 198 (SmA→SmB) | 65 (SmB→SmE) |
| 67 | 224 | — | 70 |
| 68 | 91 | 84 | 39 |
| 69 | 82 | 79 | 35 |
| 70 | 99 | 97 | 51 |
| 71 | 47 | — | 46 |
| 72 | 42 | 36 | 26 |
| 73 | (SmA, SmC on rapid cooling) | | 78 (m.p.) |
| 74 | 154 | — | 94 |
| 75 | 149 | — | 80 |
| 76 | 200 (I→N) | 187 (N→SmA) | 110 (SmC→K) |
| 77 | 193 (I→N) | 188 (N→SmA) 179 (SmA→SmC) | 96 (SmC→K) |
| 78 | 172 | 161 | 98 |
| 79 | 174 (I→N) | 172 (N→SmA) 163 (SmA→SmC) | 134 (SmC→K) |
| 80 | 135 (I→N) 132 (N→SmA) | 121 (SmA→SmC) | 102 |
| 81 | 190 | 154 | 88 |
| 82 | 145 | 127 | 107 |
| 83 | 137 | 135 | 60 |
| 84 | 165 | 145 | 40 |
| 85 | 254 | 205 | 88 |
| 86 | 238 | 170 | 136 |
| 87 | 220 | 169 | 82 |
| 88 | 151 | — | 111 |
| 89 | 205 (I→SmB) | — | 105 (SmB→K) |
| 90 | 223 | — | 200 |
| 91 | | | |
| 92 | 217 (I→N) | 212 (N→SmC) | 209 (SmC→SmB) 201 (SmB→K) |
| 93 | 204 | 185 | 179 (SmC→SmF) 133 (SmF→K) |
| 94 | 214 | 207 | 136 |
| 95 | 203 | 188 | 136 |

In the following Examples 146–152, liquid crystal electrooptical devices are described which contain the achiral, smectic liquid crystal compounds of the invention alone, mixtures of the achiral, smectic liquid crystal compounds of the invention, and mixtures of the achiral, smectic liquid crystal compounds of the invention with other liquid crystal compounds.

For example, mixtures which are smectic C and in which none of the components are chiral are useful in a device application as described by Pelzl, G., Schubert, H., Zaschke, H., and Demus, D., *Kristall Technik.*, 1979, vol 14, 817; Pelzl, G., Kolbe, P., Preukschas, U., Diele, S , and Demus, D., *Mol. Cryst. Liq Cryst.*, 1979, vol. 53, 167; Pelzl, G., Schiller, P., and Demus, D., *Liquid Crystals*, 1987, vol 2, 131; and Schiller, P., Pelzl, G., and Demus, D., *Liquid Crystals*, 1987, vol 2, 21, in which the Freedericksz effect is used.

Mixtures which are smectic C and contain a chiral dopant, i.e., a material which is optically active and which is or is not itself a liquid crystal, are ferroelectric and are useful in device applications as described by Clark and Lagerwall in U.S. Pat. No. 4,367,924.

Mixtures which exhibit a smectic A mesophase are useful in devices described by Crossland, et al. in U.S. Pat. Nos. 4,411,494, No. 4,419,664, and No. 4,528,562.

Mixtures which exhibit a smectic A mesophase and contain a chiral component are useful in a device as described by Lagerwall, et al. *1st International Symposium on Ferroelectric Liquid Crystals*, Bordeaux-Arcachon, France, 1987.

The percentages given for each of the components were determined from normalized gas chromatographs on the mixtures unless otherwise noted. The mesophases were determined by optical microscopy using a Mettler FP-5 hot stage and a Leitz polarizing microscope The transition temperatures were determined by optical microscopy using the hot stage and polarizing microscope and/or by standard differential scanning calorimetry (DSC) using a Perkin-Elmer Model DSC-4. The response times of the mixtures were measured at the rising edge of the cell photoresponse and calculated from 10–90% of the maximum transmission. The response times were measured at a voltage of 30 and at the temperatures given in each example. The polarizations were determined according to the procedure of Miyasato, et al., *Jap. J. Appl. Phys.*, vol. 22, 1983, p. 1161–1663, for the mixtures exhibiting a chiral smectic C (smectic C*) mesophase. The tilt angles of the mixtures in the smectic C(*) mesophase were determined by the technique described by Baikalov, et al., *Mol. Cryst. Liq. Cryst.*, 1985, vol. 127, pp. 397–406.

Each cell used in the liquid crystal electooptical display devices was fabricated as follows:

Two indium-tin oxide-coated glass substrates (3.49 cm×2.86 cm, 1.65 mm thick were cleaned with monoethanolamine. An electrode pattern was etched into each indium-tin oxide coating through a photolithography process. The resulting glass substrates had a conductive indium-tin oxide electrode-active area of 0.9073 cm$^{-2}$. Onto the indium-tin oxide surface of one of the substrates, a 0.5% nylon in formic acid solution was spun at 1100 r.p.m., the solvent was removed, and the nylon film (about 500 angstroms thick) was buffed with a soft roller brush for 15 minutes. The glass substrates were adhered together with indium-tin oxide surface facing indium-tin oxide surface and mylar spacers (2–4 micrometers thick) located along two opposing edges of the substrates, by a thermally-cured or u.v.-cured epoxy adhesive applied along the edges having the spacers. The cells were then filled with the specified liquid crystal material by capillary action at temperatures above the isotropic to smectic A(*) transition.

EXAMPLE 146

A mixture was prepared by mixing the following:

| | |
|---|---|
| 6-decyloxynicotinic acid 4-(1,1-dihydroperfluorohexyloxy)phenyl ester (Compound 62) | 5.14% |
| 4-octyloxybenzoic acid 4-(1,1-dihydroperfluorobutoxy)phenyl ester (Compound 18) | 9.36% |
| 4-octyloxybenzoic acid 4-(1,1-dihydroperfluorohexyloxy)phenyl ester (Compound 19) | 9.44% |
| 4-(1,1-dihydroperfluorobutoxy)benzoic acid 4-octyloxyphenyl ester (Compound 29) | 10.61% |
| 4-(4-octyloxybenzoyloxy)benzoic acid 1,1-dihydroperfluorobutoxy ester (Compound 68) | 12.42% |
| 4-(4-decyloxybenzoyloxy)benzoic acid 1,1-dihydroperfluorobutoxy ester (Compound 69) | 30.23% |
| 3-chloro-4-(1,1-dihydroperfluorohexyloxy) benzoic acid 4-decyloxyphenyl ester (Compound 41) | 22.81% |

The mixture exhibited smectic A and smectic C mesophases. Transition temperatures of the mixture were 87° C. for I→SmA, 69° C. for SmA→SmC, and at 5° C. the mixture made a transition from SmC to an unidentified high order smectic or crystalline phase. Using a field of 10 V/μm at 25° C., the mixture had a time on of 15 msec and a time off of 15 msec in the SmC mesophase. Using a field of 15 V/μm at 25° C., the mixture had a time on of 13 msec and a time off of 12 msec in the SmC mesophase. Using a field of 20 V/μm at 25° C., the mixture had a time on of 11 msec and a time off of 5 msec in the SmC mesophase.

EXAMPLE 147

A mixture was prepared by mixing together the following:

| | |
|---|---|
| 6-decyloxynicotinic acid 4-(1,1-dihydroperfluorohexyloxy)phenyl ester (Compound 62) | 4.47% |
| 4-octyloxybenzoic acid 4-(1,1-dihydroperfluorobutoxy)phenyl ester (Compound 18) | 7.98% |
| 4-octyloxybenzoic acid 4-(1,1-dihydroperfluorohexyloxy)phenyl ester (Compound 19) | 8.13% |
| 4-(1,1-dihydroperfluorobutoxy)benzoic acid 4-octyloxyphenyl ester (Compound 29) | 9.09% |
| 4-(4-octyloxybenzoyloxy)benzoic acid 1,1-dihydroperfluorobutoxy ester (Compound 68) | 10.72% |
| 4-(4-decyloxybenzoyloxy)benzoic acid 1,1-dihydroperfluorobutoxy ester (Compound 69) | 26.02% |
| 3-chloro-4-(1,1-dihydroperfluorohexyloxy)benzoic acid 4-decyloxyphenyl ester (Compound 41) | 25.27% |
| R-4-(2-fluoropropanoyloxy)phenyl 4-(1,1-dihydroperfluorobutoxy)benzoate (Prepared as in Example 133 of European Patent Publication No. 0,255,236) using R-2-fluoropropanoic acid in place of S-2-chloro-4-methylpentanoic acid) | 8.32% |

A 2.7 micrometers thick cell was filled with this mixture by capillary action. The mixture exhibited chiral smectic A and chiral smectic C mesophases. Transition temperature of the mixture were 91° C. for I→SmA*, 59° C. for SmA*→SmC*, and at 2° C. the mixture made a transition from SmC* to an unidentified high order chiral smectic or crystalline phase. Using a field of 30 V at 20° C., the mixture had a response time of 308 μsec, a polarization of 12.4 nC/cm$^{-2}$, and a tilt angle of 29°. Using a field of 30 V at 45° C., the mixture had a response time of 41 μsec, a polarization of 7.76 nC/cm$^{-2}$, and a tilt angle of 22.8°.

EXAMPLE 148

A mixture was prepared by mixing together the following:

| | |
|---|---|
| 4-octyloxybenzoic acid 4-(1,1-dihydroperfluorobutoxy)phenyl ester (Compound 18) | 15.33% |
| 4-(4-octyloxybenzoyloxy)benzoic acid 1,1-dihydroperfluorobutoxy ester (Compound 68) | 16.51% |
| 4-(4-decyloxybenzoyloxy)benzoic acid 1,1-dihydroperfluorobutoxy ester (Compound 69) | 21.08% |
| 2-chloro-4-(4-octyloxybenzoyloxy)benzoic acid 1,1-dihydroperfluorobutoxy ester (Compound 47) | 9.67% |
| 3-chloro-4-(1,1-dihydroperfluorohexyloxy)benzoic acid 4-octyloxyphenyl ester (Compound 43) | 37.41% |

The mixture exhibited smectic A and smectic C mesophases. Transition temperatures of the mixture were 88° C. for I→SmA, 69° C. for SmA→SmC, and at −9° C. the mixture made a transition from SmC to an unidentified high order smectic or crystalline phase.

EXAMPLE 149

A mixture was prepared by mixing together the following:

| | |
|---|---|
| 4-octyloxybenzoic acid 4-(1,1-dihydroperfluorobutoxy)phenyl ester (Compound 18) | 14.88% |
| 4-(4-octyloxybenzoyloxy)benzoic acid 1,1-dihydroperfluorobutoxy ester (Compound 68) | 14.56% |
| 4-(4-decyloxybenzoyloxy)benzoic acid 1,1-dihydroperfluorobutoxy ester (Compound 69) | 18.29% |

| | |
|---|---|
| 2-chloro-4-(4-octyloxybenzoyloxy)benzoic acid 1,1-dihydroperfluorobutoxy ester (Compound 47) | 11.73% |
| 3-chloro-4-(1,1-dihydroperfluorohexyloxy)benzoic acid 4-octyloxyphenyl ester (Compound 43) | 31.28% |
| S-4-(2-chloro-4-methylpentanoyloxy)phenyl 4-(1,1-dihydroperfluorohexyloxy)benzoate (Prepared as in Example 133 of European Patent Publication No. 0,255,236) | 9.27% |

A 2.7 micrometers thick cell was filled with this mixture by capillary action. The mixture exhibited chiral smectic A and chiral smectic C mesophases. Transition temperatures of the mixture were 85° C. for I→SmA*, 65° C. for SmA*→SmC*, and at −13° C. the mixture made a transition from SmC* to an unidentified high order chiral smectic or crystalline phase. Using a field of 30 V at 25° C., the mixture had a response time of 148 μsec, a polarization of 8.9 nC/cm⁻², and a tilt angle of 30.2°. Using a field of 30 V at 45° C., the mixture had a response time of 37 μsec and a tilt angle of 30.0°.

EXAMPLE 150

A mixture was prepared by mixing together the following:

| | |
|---|---|
| 4-octyloxybenzoic acid 4-(1,1-dihydroperfluorobutoxy)phenyl ester (Compound 18) | 13.36% |
| 4-(4-octyloxybenzoyloxy)benzoic acid 1,1-dihydroperfluorobutoxy ester (Compound 68) | 13.14% |
| 4-(4-decyloxybenzoyloxy)benzoic acid 1,1-dihydroperfluorobutoxy ester (Compound 69) | 16.97% |
| 2-chloro-4-(4-octyloxybenzoyloxy)benzoic acid 1,1-dihydroperfluorobutoxy ester (Compound 47) | 10.78% |
| 3-chloro-4-(1,1-dihydroperfluorohexyloxy)benzoic acid 4-octyloxyphenyl ester (Compound 43) | 28.31% |
| S-4-(2-chloro-4-methylpentanoyloxy)phenyl 4-(1,1-dihydroperfluorohexyloxy)benzoate (Prepared as in Example 133 of European Patent Publication No. 0,255,236) | 17.44% |

A 2.7 micrometers thick cell was filled with this mixture by capillary action. The mixture exhibited chiral smectic A and chiral smectic C mesophases. Transition temperatures of the mixture were 83° C. for I→SmA*, 61° C. for SmA*→SmC*, and at −13° C. the mixture made a transition from SmC* to an unidentified high order chiral smectic or crystalline phase. Using a field of 30 V at 25° C., the mixture had a response time of 81 μsec, a polarization of 26.0 nC/cm⁻², and a tilt angle of 34.5°. Using a field of 30 V at 45° C., the mixture had a response time of 19 μsec and a tilt angle of 32.0°.

EXAMPLE 151

A mixture was prepared by mixing together the following:

| | |
|---|---|
| 6-decyloxynicotinic acid 4-(1,1-dihydroperfluorohexyloxy)phenyl ester (Compound 62) | 5.09% |
| 4-octyloxybenzoic acid 4-(1,1-dihydroperfluorobutoxy)phenyl ester (Compound 18) | 9.04% |
| 4-octyloxybenzoic acid 4-(1,1-dihydroperfluorohexyloxy)phenyl ester (Compound 19) | 9.30% |
| 4-(1,1-dihydroperfluorobutoxy)benzoic acid 4-octyloxyphenyl ester (Compound 29) | 10.06% |
| 4-(4-octyloxybenzoyloxy)benzoic acid 1,1-dihydroperfluorobutoxy ester (Compound 68) | 11.22% |
| 4-(4-decyloxybenzoyloxy)benzoic acid 1,1-dihydroperfluorobutoxy ester (Compound 69) | 28.32% |
| 3-chloro-4-(1,1-dihydroperfluorohexyloxy)benzoic acid 4-decyloxyphenyl ester (Compound 41) | 21.04% |
| S-2-methylbutyl 4-(4'-octyloxybenzoyloxy) benzoate (Described by J. W. Goodby and T. M. Leslie in Liquid Crystals and Ordered Fluids, vol. 4, pp 1–42, edited by A. C. Griffin and J. F. Johnson.) | 5.92% |

A 2.9 micrometers thick cell was filled with this mixture by capillary action. The mixture exhibited chiral smectic A and chiral-smectic C mesophases. Transition temperatures of the mixture were 87° C. for I→SmA*, 68° C. for SmA*→SmC*, and at 2° C. the mixture made a transition from SmC* to an unidentified high order chiral smectic or crystalline phase. Using a field of 30 V/um at 25° C., the mixture had a response time of 250 μsec and a polarization of >1 nC/cm⁻².

EXAMPLE 152

A mixture was prepared by mixing together the following:

| | |
|---|---|
| 6-decyloxynicotinic acid 4-(1,1-dihydroperfluorohexyloxy)phenyl ester (Compound 62) | 4.85% |
| 4-octyloxybenzoic acid 4-(1,1-dihydroperfluorobutoxy)phenyl ester (Compound 18) | 8.79% |
| 4-octyloxybenzoic acid 4-(1,1-dihydroperfluorohexyloxy)phenyl ester (Compound 19) | 8.96% |
| 4-(1,1-dihydroperfluorobutoxy)benzoic acid 4-octyloxyphenyl ester (Compound 29) | 9.78% |
| 4-(4-octyloxybenzoyloxy)benzoic acid 1,1-dihydroperfluorobutoxy ester (Compound 68) | 10.83% |
| 4-(4-decyloxybenzoyloxy)benzoic acid 1,1-dihydroperfluorobutoxy ester (Compound 69) | 26.06% |
| 3-chloro-4-(1,1-dihydroperfluorohexyloxy)benzoic acid 4-decyloxyphenyl ester (Compound 41) | 19.58% |
| R-1-methylheptyl 4-(4'-(1,1-dihydroperfluorobutoxy)benzoyloxy)benzoate (Prepared as in Example 88 of European Patent Publication No. 0,255,236) using R-1-methylheptyl 4-hydroxybenzoate in place of S-2-methylbutyl 4-hydroxybenzoate | 11.15% |

A 2.8 micrometers thick cell was filled with this mixture by capillary action. The mixture exhibited chiral smectic A and chiral smectic C mesophases. Transition temperatures of the mixture were 80° C. for I→SmA*, 63° C. for SmA*→SmC*, and at 2° C. the mixture made a transition from SmC* to an unidentified high order chiral smectic or crystalline phase. Using a field of 30 V at 35° C., the mixture had a response time of 40 μsec, a polarization of 22.9 nC/cm⁻², and a tilt angle of 30.6°.

In the following Tables III-IX, comparisons are made of the mesophases exhibited by selected compounds of the invention and the hydrocarbon analogs. The mesophases for the hydrocarbon analogs were obtained from Demus, Demus, and Zaschke, *Flussige Kristalle in Tabellen*, VEB Deutscher Verlag fur Grundstoffindustrie, Leipzig, 1974, and Demus and Zaschke, *Flussige Kristalle in Tabellen II*, VEB Deutscher Verlag fur Grundstoffindustrie, Leipzig, 1984.

The compounds of Table III can be represented by the formula

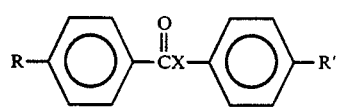

where R, R', and X are set forth in the table. The compound numbers are also set forth in Table III for the compounds of the invention.

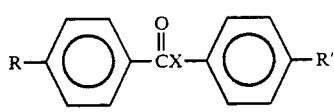

The compounds of Table IV can be represented by the formula

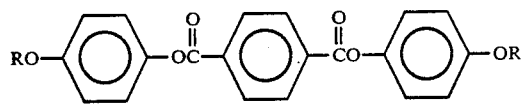

where R is as set forth in the table. The compound numbers are also set forth in Table IV for the compounds of the invention.

TABLE IV

| R | Cmpd No. | Mesophases |
|---|---|---|
| $C_4H_9-$ | — | N |
| $C_3F_7CH_2-$ | 94 | SmA, SmC |
| $C_6H_{13}-$ | — | N |
| $C_5F_{11}CH_2-$ | 95 | SmA, SmC |

The compounds of Table V can be represented by the formula

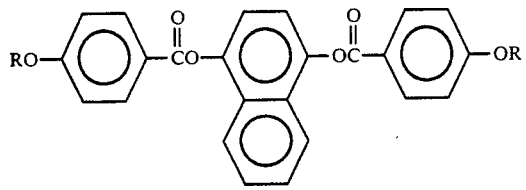

where R is as set forth in Table V. The compound numbers are also set forth in Table V for the compounds of the invention.

TABLE V

| R | Cmpd No. | Mesophases |
|---|---|---|
| $C_4H_9-$ | — | N |
| $C_3F_7CH_2-$ | 90 | SmA |

The compounds of Table VI can be represented by the formula

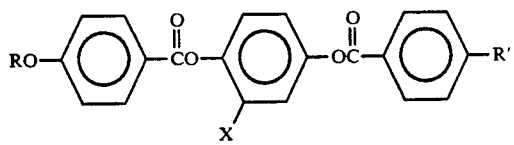

where R, R', and X are as set forth in the table. The compound numbers are also set forth in Table VI for the compounds of the invention.

TABLE VI

| R | R' | X | Cmpd No. | Mesophases |
|---|---|---|---|---|
| $C_4H_9-$ | $-OC_4H_9$ | H | — | N |
| $C_3F_7CH_2-$ | $-OCH_2C_3F_7$ | H | 86 | SmA, SmC |
| $C_4H_9-$ | $-OC_8H_{17}$ | H | — | N |
| $C_3F_7CH_2-$ | $-OC_8H_{17}$ | H | 76 | N, SmA, SmC |

TABLE VI-continued

| R | R' | X | Cmpd No. | Mesophases |
|---|---|---|---|---|
| $C_3F_7CH_2-$ | $-OCH_2C_7F_{15}$ | H | 85 | SmA, SmC |
| $C_4H_9-$ | $-C_{10}H_{21}$ | H | — | N |
| $C_3F_7CH_2-$ | $-C_{10}H_{21}$ | H | 78 | SmA, SmC |
| $C_3H_7-$ | $-OC_3H_7$ | $CH_3$ | — | N |
| $C_2F_5CH_2-$ | $-OCH_2C_2F_5$ | $CH_3$ | 88 | SmA |
| $C_6H_{13}-$ | $-OC_6H_{13}$ | Cl | — | N |
| $C_5F_{11}CH_2-$ | $-OCH_2C_5F_{11}$ | Cl | 87 | SmA, SmC |

The compounds of Table VII can be represented by the formula

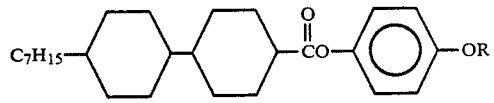

where R is as set forth in Table VII. The compound number is also set forth in Table VII for the compound of the invention.

TABLE VII

| R | Cmpd No. | Mesophases |
|---|---|---|
| $C_6H_{13}-$ | — | N |
| $C_5F_{11}CH_2-$ | 55 | SmA, SmB |

The compounds of Table VIII can be represented by the formula

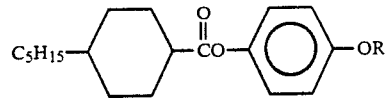

where R is as set forth in Table VIII. The compound number is also set forth in Table VIII for the compound of the invention.

TABLE VIII

| R | Cmpd No. | Mesophases |
|---|---|---|
| $C_6H_{13}-$ | — | N, SmA, SmC |
| $C_5F_{11}CH_2-$ | 53 | SmA, SmC |

The compounds of Table IX can be represented by the formula

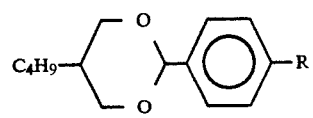

where R is as set forth in the table. The compound numbers are also set forth in Table IX for the compounds of the invention.

TABLE IX

| R | Cmpd No. | Mesophases |
|---|---|---|
| $C_6H_{13}O-$ | — | N |
| $C_5F_{11}CH_2O-$ | 65 | SmA |

TABLE IX-continued

| R | Cmpd No. | Mesophases |
|---|---|---|
| $C_6H_{13}O$—⬡—O—C(=O)— | — | N |
| $C_5F_{11}CH_2O$—⬡—O—C(=O)— | 67 | SmA |

Various modifications and alterations of this invention will become apparent to those skilled in the art without departing from the scope and spirit of this invention, and it should be understood that this invention is not to be unduly limited to the following illustrative embodiments set forth herein.

What is claimed is:

1. A chiral fluorine-containing liquid crystal compounds comprising a fluorocarbon terminal portion represented by the formula $-DC_qF_{2q}X$ where X is hydrogen or fluorine, q is 1-20, and D is $$-\overset{O}{\underset{\|}{C}}-O-(CH_2)_r-,\ -O-(CH_2)_r-,\ -(CH_2)_r-,\ -OSO_2-,$$

$$-SO_2-,\ -SO_2(CH_2)_r-,\ -O(CH_2)_r-O(CH_2)_{r'}-,$$

$$-(CH_2)_r-\underset{C_pH_{2p+1}}{\overset{|}{N}}-SO_2-,\text{ or }-(CH_2)_r-\underset{C_pH_{2p+1}}{\overset{|}{N}}-\overset{O}{\underset{\|}{C}}-$$

where r and r' are independently 1 to 20 and p is 0 to 4, and a hydrocarbon or another fluorocarbon terminal portion, the terminal portions being connected by a central core, the compounds having smectic mesophases or having latent smectic mesophases.

2. The compounds of claim 1 wherein said central core comprises at least two aromatic, heteroaromatic, cycloaliphatic, or substituted aromatic, heteroaromatic, or cycloaliphatic rings.

3. The compounds of claim 2 wherein rings are connected one with another by —COO—, —COS—, —HC=N—, or —COSe—.

4. The compounds of claim 2 wherein heteroatoms within the heteroaromatic ring are N, O, or S.

5. The compounds of claim 1 wherein said compounds can be represented by the general formula I:

$$R-(M-)_aA-(N)_bB-(P)-_cD-R_f \quad (I)$$
$$\phantom{R-(M-)_a}\underset{X_l}{|}\phantom{A-(N)_b}\underset{Y_m}{|}\phantom{B-(P)}\underset{Z_n}{|}$$

where
M, N, and P are each independently

[cyclohexane, benzene, naphthalene, naphthalene (isomer), tetralin, pyridine, pyridazine, pyrimidine, dioxane ring structures]

a, b, and c are independently zero or an integer of from 1 to 3 with the proviso that the sum of a+b+c be at least 2;

each A and B are non-directionally and each independently a covalent bond, $$-\overset{O}{\underset{\|}{C}}-O-,\ -\overset{O}{\underset{\|}{C}}-S-,\ -\overset{O}{\underset{\|}{C}}-Se$$

$$-\overset{O}{\underset{\|}{C}}-Te-,\ -CH_2CH_2-,\ -CH=CH-,\ -C\equiv C-,$$

$$-CH=N-,\ -CH_2-O-,\ -CO-\text{ or }-O-;$$

each X, Y, and Z are independently —H, —Cl, —F, —Br, —I, —OH, —OCH$_3$, —CH$_3$, —CN, or —NO$_2$;

each l, m, and n are independently zero or an integer of 1 to 4, $$D\text{ is }-\overset{O}{\underset{\|}{C}}-O-(CH_2)_r-,\ -O-(CH_2)_r-,\ -(CH_2)_r-,$$

$$-OSO_2-,\ -SO_2-,\ -SO_2-(CH_2)_r-,$$

$$-O(CH_2)_r-O-(CH_2)_{r'}-,\ -(CH_2)_r-\underset{C_pH_{2p+1}}{\overset{|}{N}}-SO_2-,\text{ or}$$

$$-(CH_2)_r-\underset{C_pH_{2p+1}}{\overset{|}{N}}-CO-$$

where r and r' are independently 1 to 20, and p is 0 to 4;
r is .

$$-O-C_qH_{2q}-O-C_{q'}H_{2q'+1},\ -C_qH_{2q}-O-C_{q'}H_{2q'+1},$$

$$-C_qH_{2q}-R',\ -O-C_qH_{2q}-R',\ -\overset{O}{\underset{\|}{C}}-O-C_qH_{2q}-R',$$

$$\text{or }-O-\overset{O}{\underset{\|}{C}}-C_qH_{2q}-R',$$

where R' is

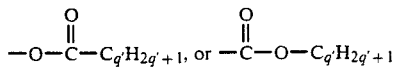

and q and q' are independently 1 to 20, and R can be straight chain or branched, and $R_f$ is $C_qF_{2q}$-X where X is H or F, and q and q' are independently 1 to 20.

6. The compounds of claim 1 wherein said compounds exhibit birefringences in the range of 0.05-0.18.

7. The compounds of claim 1 wherein said compounds having smectic mesophases have suppressed nematic mesophases.

8. The compounds according to claim 1 wherein said compounds exhibit rise and decay times of less than 1 millisecond have been observed for an 80% change in the light intensity in smectic C Freedericksz-type liquid crystal display devices.

9. Mixtures of two or more of the compounds of claim 1, at least one of said compounds having smectic mesophases.

10. Liquid crystal mixtures comprising at least one compound according to claim 1 and at least one chiral liquid crystal compound.

11. The liquid crystal mixtures of claim 10 wherein said chiral liquid crystal compound is present in an amount sufficient to provide the mixture with ferroelectric properties.

12. The liquid crystal mixtures of claim 11 wherein said chiral liquid crystal compound is present in an amount of about 1 to 25 weight percent.

13. Liquid crystal mixtures comprising at least one compound according to claim 1 and at least one non-liquid crystal compound.

14. The liquid crystal mixtures of claim 10 wherein said non-liquid crystal compound is present in an amount sufficient to provide the mixture with ferroelectric properties.

15. A liquid crystal display device containing said compound of claim 1 wherein said compound has a smectic mesophase.

16. A liquid crystal display device containing the mixture of claim 9.

17. A liquid crystal display device containing the mixture of claim 10.

18. A liquid crystal display device containing the mixture of claim 11.

* * * * *

UNITED STATES PATENT AND TRADEMARK OFFICE
CERTIFICATE OF CORRECTION

PATENT NO. : 5,082,587
DATED : January 21, 1992
INVENTOR(S) : Eugene P. Janulis It is certified that error appears in the above-identified patent and that said Letters Patent is hereby corrected as shown below:

On the title page item:

[76] Inventor: Delete "3M Center, P.O. Box 34427, St. Paul, Minn. 55133-3727" and insert -- Mahtomedia, Minn. --

[57] Abstract
Line 8                  "along" should read -- alone --

Col. 2, line 15         insert ":" after "applications"

Col. 3, line 33         "for" should read -- or --

Col. 4, line 24         "—the," should read -- —TeH, --

Col. 4, lines 55 and 60     " —CH$_2$)," should read -- —(CH$_2$), --

Col. 6, line 48         "are" should read -- as --

Col. 8, line 19         " $\Delta$ " should read -- $\lambda$ --

Col. 8, line 22         "sin$^2$($\pi$nd/$\lambda$)" should read -- sin$^2$($\pi\Delta$nd/$\lambda$) --

Col. 9, line 7          "645-5,656" should read -- 645-6, 656 --

Col. 9, lines 22, 24, 25, 34, 36, 62     "trans" should read -- *trans* --

UNITED STATES PATENT AND TRADEMARK OFFICE
CERTIFICATE OF CORRECTION

PATENT NO. : 5,082,587

DATED : January 21, 1992

INVENTOR(S) : Eugene P. Janulis

It is certified that error appears in the above-identified patent and that said Letters Patent is hereby corrected as shown below:

| | |
|---|---|
| Col. 9, line 48 | "[4-cyano-4 -decylbiphenyl]" should read --[4-cyano-4'-decylbiphenyl] -- |
| Col. 11, line 2 | "(1,87" should read -- (1.87 -- |
| Col. 12, line 68 | "monobenzylhydroqunnone" should read -- monobenzylhydroquinone -- |
| Col. 15, line 14 | "dl-4-methylhexanol" should read -- _dl_-4-methylhexanol -- |
| Col. 15, line 15 | "dl-6-(4-methylhexyloxy)nicotinic" should read -- _dl_-6-(4-methylhexyloxy)nicotinic -- |
| Col. 15, line 19 | "(1 44" should read -- (1.44 -- |
| Col. 15, lines 28 and 40 | "ml" should read -- mL |
| Col. 20, line 40 | "4,-(1,1-dihy-" should read -- 4'-(1,1-dihy- -- |
| Col. 21, line 3 | "trans-" should read -- _trans_ -- |
| Col. 21, line 4 | ". . .phenyl) -1,3-dioxane," should read -- . . . phenyl)-1,3-dioxane, -- |
| Col. 21, line 9 | "Trans-" should read -- _Trans-_ -- |

UNITED STATES PATENT AND TRADEMARK OFFICE
CERTIFICATE OF CORRECTION

PATENT NO. : 5,082,587
DATED : January 21, 1992
INVENTOR(S) : Eugene P. Janulis

It is certified that error appears in the above-identified patent and that said Letters Patent is hereby corrected as shown below:

Col. 23, line 6   "4-!,!-dihydroperfluorobutoxy)benzo-"
                    should read
            -- 4-1,1-dihydroperfluorobutoxy)benzo- --

Cols. 35-36  Insert at the top of columns 35 and 36, the attached sheet consisting of examples 65-75.

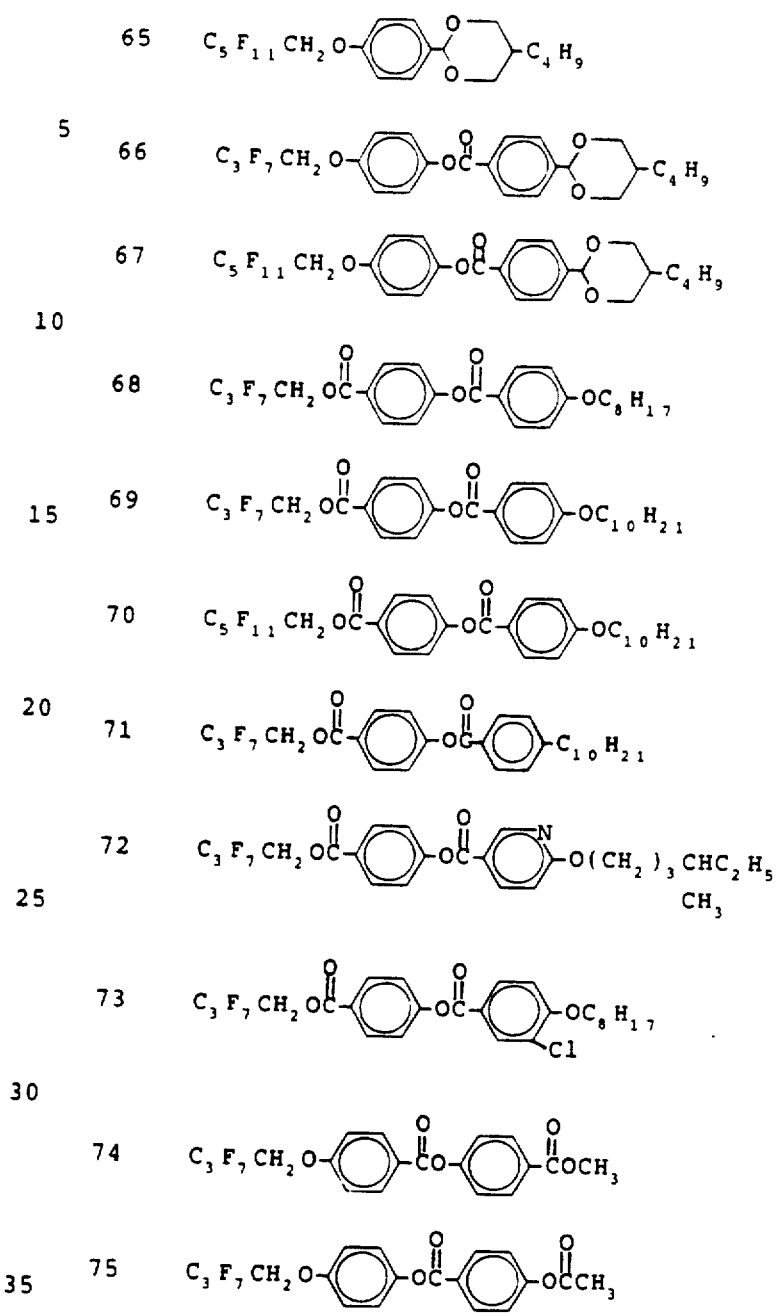

UNITED STATES PATENT AND TRADEMARK OFFICE
CERTIFICATE OF CORRECTION

PATENT NO. : 5,082,587

DATED : January 21, 1992

INVENTOR(S) : Eugene P. Janulis

It is certified that error appears in the above-identified patent and that said Letters Patent is hereby corrected as shown below:

Col. 41, line 14    "1161-1663," should read -- 1661-1663, --

Col. 44, line 14    "V/um" should read -- V --

Col. 45, lines 1-5  delete the chemical drawing and replace it with Table III as shown on attached sheet.

Table III

| R | R' | X | Cmpd No. | Mesophases |
|---|---|---|---|---|
| $C_4H_9O-$ | $-C_6H_{13}$ | S | - | N |
| $C_3F_7CH_2O-$ | $-C_6H_{13}$ | S | 2 | SmA, SmC |
| $C_4H_9O-$ | $-OC_6H_{13}$ | S | - | N |
| $C_3F_7CH_2-$ | $-OC_6H_{13}$ | S | 1 | SmA, SmC |
| $C_4H_9O-$ | $-OC_6H_{13}$ | O | - | N |
| $C_3F_7CH_2O-$ | $-OC_6H_{13}$ | O | 27 | SmA, SmC |
| $C_4H_9O-$ | $-OCH_2C_5F_{11}$ | O | 14 | SmA |
| $C_4H_9O-$ | $-OC_7H_{15}$ | O | - | N |
| $C_3F_7CH_2O-$ | $-OC_7H_{15}$ | O | 28 | SmA, SmC |
| $C_4H_9O-$ | $-OC_8H_{17}$ | O | - | N |
| $C_3F_7CH_2O-$ | $-OC_8H_{17}$ | O | 29 | SmA, SmC |
| $C_4H_9O-$ | $-OC_{10}H_{21}$ | O | - | N |
| $C_3F_7CH_2O-$ | $-OC_{10}H_{21}$ | O | 30 | SmA, SmC |
| $C_6H_{13}O-$ | $-OC_6H_{13}$ | O | - | N |
| $C_5F_{11}CH_2O-$ | $-OC_6H_{13}$ | O | 32 | SmA, SmC |
| $C_6H_{13}O-$ | $-OCH_2C_5F_{11}$ | O | 16 | SmA, SmC |
| $C_6H_{13}O-$ | $-OC_8H_{17}$ | O | - | N |
| $C_5F_{11}CH_2O-$ | $-OC_8H_{17}$ | O | 34 | SmA, SmC |
| $C_6H_{13}O-$ | $-OCH_2C_7F_{15}$ | O | 17 | SmA, SmC |
| $C_{10}H_{21}O-$ | $-OC_6H_{13}$ | O | - | N, SmA, SmC, SmB |
| $C_{10}H_{21}O-$ | $-OCH_2C_5F_{11}$ | O | 6 | SmA, SmC |
| $C_{10}H_{21}O-$ | $-OCH_2CH_2C_4F_9$ | O | 8 | SmA, SmC |
| $C_{10}H_{21}O-$ | $-OCH_2(CF_2)_4H$ | O | 10 | SmA, SmC |
| $C_4H_9O-$ | $-CN$ | O | - | N |
| $C_3F_7CH_2O-$ | $-CN$ | O | 50 | SmA |
| $C_8H_{17}O-$ | $-OC_6H_{13}$ | O | - | N, SmC |
| $C_7F_{15}CH_2O-$ | $-OC_6H_{13}$ | O | 36 | SmA, SmC |
| $C_8H_{17}O-$ | $-OCH_2C_5F_{11}$ | O | 19 | SmA, SmC |
| $C_8H_{17}O-$ | $-OC_8H_{17}$ | O | - | N, SmC |
| $C_7F_{15}CH_2O-$ | $-OC_8H_{17}$ | O | 37 | SmA, SmC |
| $C_8H_{17}O-$ | $-OCH_2C_7F_{15}$ | O | 20 | SmA, SmC |
| $C_8H_{17}O-$ | $-OC_{10}H_{21}$ | O | - | N, SmC |
| $C_7F_{15}CH_2O-$ | $-OC_{10}H_{21}$ | O | 38 | SmA, SmC |

UNITED STATES PATENT AND TRADEMARK OFFICE
CERTIFICATE OF CORRECTION

PATENT NO. : 5,082,587

DATED : January 21, 1992

INVENTOR(S) : Eugene P. Janulis

It is certified that error appears in the above-identified patent and that said Letters Patent is hereby corrected as shown below:

Col. 47, line 22    "A chiral" should read -- Achiral --

Col. 48, line 57    "r" should read -- R --

Col. 48, line 69    at end of line, after "is", insert: -- -Cl. -F, -CF$_3$, -NO$_2$, -CN, -H, --

Signed and Sealed this

Nineteenth Day of October, 1993

*Attest:*

BRUCE LEHMAN

*Attesting Officer*   Commissioner of Patents and Trademarks